US012116415B2

(12) United States Patent
Tang et al.

(10) Patent No.: US 12,116,415 B2
(45) Date of Patent: Oct. 15, 2024

(54) ANTI-BCMA ANTIBODIES

(71) Applicants: Single Cell Technology, Inc., San Jose, CA (US); ACROBiosystems, Inc., Beijing (CN)

(72) Inventors: Leyan Tang, San Jose, CA (US); Allison Schulkins, San Jose, CA (US); Kimberly Than, San Jose, CA (US); Chun-Nan Chen, San Jose, CA (US); Jingyun Miao, Beijing (CN); Xiaohui Zhang, Beijing (CN); Xiaojuan Shi, Beijing (CN); Lin Zhang, Beijing (CN)

(73) Assignees: Single Cell Technology, Inc., San Jose, CA (US); ACROBiosystems, Inc., Beijing (CN)

( * ) Notice: Subject to any disclaimer, the term of this patent is extended or adjusted under 35 U.S.C. 154(b) by 759 days.

(21) Appl. No.: 17/284,371

(22) PCT Filed: Oct. 9, 2019

(86) PCT No.: PCT/CN2019/110114
§ 371 (c)(1),
(2) Date: Apr. 9, 2021

(87) PCT Pub. No.: WO2020/073917
PCT Pub. Date: Apr. 16, 2020

(65) Prior Publication Data
US 2021/0332145 A1    Oct. 28, 2021

Related U.S. Application Data

(60) Provisional application No. 62/743,413, filed on Oct. 9, 2018.

(51) Int. Cl.
| C07K 16/28 | (2006.01) |
| A61K 39/395 | (2006.01) |
| A61K 47/68 | (2017.01) |
| G01N 33/53 | (2006.01) |

(52) U.S. Cl.
CPC ........ *C07K 16/2878* (2013.01); *A61K 39/395* (2013.01); *A61K 47/6851* (2017.08); *G01N 33/53* (2013.01); *C07K 2317/565* (2013.01)

(58) Field of Classification Search
CPC .......... C07K 16/2878; C07K 2317/565; C07K 2317/33; C07K 2317/732; C07K 2317/92; A61K 47/6803; A61K 47/6851; A61K 39/395; A61P 35/00; G01N 33/53
See application file for complete search history.

(56) References Cited

U.S. PATENT DOCUMENTS 7,112,421 B2    9/2006  Ambrose et al.
9,304,138 B2 *  4/2016  Pfeifer ............... A61P 21/02
9,328,172 B2    5/2016  Chen et al.
9,732,156 B2 *  8/2017  Adamkewicz ........ A61P 21/00
10,072,088 B2   9/2018  Pillarisetti et al.

FOREIGN PATENT DOCUMENTS

| CN | 103562225 A | 2/2014 |
| CN | 108395478 A | 8/2018 |
| WO | WO-2012/163805 A1 | 12/2012 |

OTHER PUBLICATIONS

Better et al., "*Escherichia coli* Secretion of an Active Chimeric Antibody Fragment", Science 240:1041-1043 (1988).
Chiu et al., "Hodgkin lymphoma cells express TACI and BCMA receptors and generate survival and proliferation signals in response to BAFF and APRIL", Blood 109(2):729-39 (2007).
Hatzoglou et al., "TNF receptor family member Bcma (B cell maturation) associates with TNF receptor- associated factor (TRAP) 1, TRAF2, and TRAF3 and activates NF-KB, Elk-1, c-Jun N-terminal kinase, and p38 mitogen-activated protein kinase", J. Immunol. 165(3): 1322-30 (2000).
He et al., "Lymphoma B cells evade apoptosis through the TNF family members BAFF/BLyS and April", J. Immunol. 172(5):3268-79 (2004).
Huang et al., "Homeostatic cell-cycle control by BLyS: Induction of cell-cycle entry but not GI/S transition in opposition to p18INK4c and p27Kip1", Proc. Natl. Acad. Sci. U.S.A. 101(51): 17789-94 (2004).
International Search Report, dated Jan. 16, 2020, issued in corresponding International Patent Application No. PCT/CN2019/110114.
Kalled et al., "The biochemistry and biology of Baff, April and their receptors", Curr. Dir. Autoimmun. 8:206-42 (2005).
Litinskiy et al., "DCs induce CD40-independent immunoglobulin class switching through BLyS and APRIL", Nat. Immunol. 3(9):822-9 (2002).
Liu et al., "Chimeric mouse-human IgG1 antibody that can mediate lysis of cancer cells", Proc Natl Acad Sci USA 84:3439-3443 (1987).
Novak et al., "Expression of Bcma, Taci, and BAFF-R in multiple myeloma: a mechanism for growth and survival", Blood 103(2):689-94 (2004).
Novak et al., "Expression of BLyS and its receptors in B-cell non-Hodgkin lymphoma: correlation with disease activity and patient outcome", Blood 104(8): 2247-53 (2004).
O'Connor et al., "BCMA is essential for the survival of long-lived bone marrow plasma cells", J. Exp. Med. 199(1):91-8 (2004).
Pomerantz et al., "Two pathways to NF-KB", Mol. Cell 10(4):693-5 (2002).

(Continued)

*Primary Examiner* — Hong Sang
*Assistant Examiner* — Carol Ann Chase
(74) *Attorney, Agent, or Firm* — Foley & Lardner LLP

(57) ABSTRACT

Provided are antibodies that recognize the B-Cell Maturation Antigen (BCMA) and methods of use thereof.

20 Claims, 3 Drawing Sheets

Specification includes a Sequence Listing.

(56) References Cited

OTHER PUBLICATIONS

Schiemann et al., "An essential role for BAFF in the normal development of B cells through a BCMA-independent pathway", Science 293(5537):2111-4 (2001).
Written Opinion, dated Jan. 16, 2020, issued in corresponding International Patent Application No. PCT/CN2019/110114.
Xu et al., "B-cell maturation protein, which binds the tumor necrosis factor family members BAFF and APRIL, is dispensable for humoral immune responses", Mol. Cell. Biol. 21(12):4067-74 (2001).

* cited by examiner (SCT-Aa2(m/m))

ANTI-BCMA ANTIBODIES

CROSS-REFERENCE TO RELATED APPLICATIONS

This application a U.S. national stage application under 35 U.S.C. § 371 of International Application No. PCT/CN2019/110114, filed Oct. 9, 2019, which in turn claims the benefit under 35 U.S.C. § 119(e) of U.S. Provisional Application No. 62/743,413 filed Oct. 9, 2018, the contents of each of which are incorporated herein into this application by reference in its entirety for all purposes.

INCORPORATION OF SEQUENCE LISTING

The instant application contains a Sequence Listing that is filed herewith by electronic submission and is hereby incorporated by reference in its entirety. The ASCII copy, created on 8 Oct. 2019 is named SCT0004-401-PC_Sequence_Listing_ST25.txt, and is 54,800 bytes in size.

BACKGROUND

B-cells are lymphocytes that play major roles in adaptive humoral immunity and production of antibodies that specifically recognize antigens. Three subclasses of B-cells are naïve B-cells, memory B-cells, and plasma cells. The processes of VDJ recombination, in which two or three segments of DNA are chosen from a genomic library and recombined to generate a combinatorial array of antibody variable domains, and hypermutation, by which the variable domains encoded by different lineages of B-cells are further varied, result in up to 109 distinct B-cell lineages that produce antibodies with specificity for distinct targets. A B-cell is said to be specific for an antigen that binds the antibodies made by that B-cell. B-cells in general are stimulated by exposure to their specific antigen (Ag). Naïve B-cells have not yet been exposed to their specific antigen. Such exposure (e.g., during an infection) results in proliferation of B-cells and generation of sister clones. Sister clones can develop into plasma cells, which produce high amounts of antibody. Plasma cells may either be short lived, or may migrate into bone marrow, where they can persist for an extended period of time. A sister clone of an Ag-exposed B-cell may also develop into a memory B-cell that is quiescent until re-exposed to the specific antigen. Memory B-cells respond rapidly to re-exposure to antigen by dividing to produce both plasma cells and additional memory B-cells.

Several significant diseases involve B-cells. Malignant transformation of B-cells leads to cancers, including some lymphomas such as, for example, multiple myeloma and Hodgkin's Lymphoma. Some autoimmune diseases, including systemic lupus erythematosus (SLE), also involve B-cells. Both cancer and autoimmune diseases that involve B-cells may be considered gain of function conditions, in that the B-cells overgrow and/or attack parts of the body inappropriately. A possible strategy to control such diseases is to use antibodies that target the pathological B-cells.

The B-cell Maturation Antigen (BCMA, also known as TNFRSF17 and CD269) is a protein that has been shown to be expressed on the surface of plasmablasts (i.e., plasma cell precursors) and plasma cells, and is believed to stimulate survival. It therefore represents a potential target for B-cell-related diseases. BCMA is a member of the TNF receptor family and binds the TNF family ligands BAFF and APRIL (Kalled et al., 2005). BCMA is a type III membrane protein, as it lacks the signal peptide associated with type I membrane proteins found in most TNF receptor family members.

The mechanism of action of BCMA is not fully understood. Mice that have been genetically altered to lack a functional gene for BCMA have normal lymphoid organs and cell populations, and a nearly normal functioning immune system (Xu and Lam, 2001; Schiemann et al., 2001). The only defect defined to date in these mice is a diminished survival of long-lived bone marrow (BM) plasma cells (O'Connor et al., 2004). Therefore, it may be that BCMA, at least in the murine system, provides a survival signal to BM-resident plasma cells that is either BAFF or APRIL-mediated, or both. Indeed, signaling through BCMA activates the NF-κB pathway (Hatzoglou et al., 2000) which is involved in B-cell survival, proliferation and maturation (Litinskiy et al., 2002; Pomerantz and Baltimore, 2002; Huang et al., 2004; He et al., 2004). Results with malignant human cells are generally consistent with a link between BCMA and cell survival. Primary multiple myeloma (MM) cells, MM cell lines (Novak et al., 2004a), and Hodgkin and Reed-Sternberg (HRS) cells from Hodgkin lymphomas (Chiu et al., 2007; Novak et al., 2004b) have been shown to express BCMA. Addition of BAFF and/or APRIL has further been shown to provide a survival signal for these malignant cells, although it is not clear that BCMA is predominantly responsible for this effect.

Because different B-cell subsets are implicated in different B-cell related conditions, there exists a need for agents that specifically target one or more B-cell subsets. The expression of BCMA on the surface of some B-cells provides a marker by which those cells may be specifically targeted. To take advantage of BCMA as a marker of one or more B-cell subsets, there is a need for agents that specifically bind to BCMA. The disclosure provides antibodies that specifically bind to BCMA. The antibodies of the disclosure may be used to target one or more of the following B-cell subsets: plasma cells, memory B-cells, and naïve B-cells, for therapeutic applications.

BRIEF DESCRIPTION OF THE SEQUENCES

TABLE 1

| SEQ ID NO. | Description of sequence |
|---|---|
| 1 | Human BCMA protein sequence |
| 2 | Human BCMA His-tagged protein sequence |
| 3 | Human BCMA-Human Fc-tagged protein sequence |
| 4 | SCT-Aa01 mature heavy chain variable domain protein sequence |
| 5 | SCT-Aa01 mature light chain variable domain protein sequence |
| 6 | SCT-Aa02 mature heavy chain variable domain protein sequence |
| 7 | SCT-Aa02 mature light chain variable domain protein sequence |
| 8 | SCT-Aa03 mature heavy chain variable domain protein sequence |
| 9 | SCT-Aa03 mature light chain variable domain protein sequence |
| 10 | SCT-Aa04 mature heavy chain variable domain protein sequence |
| 11 | SCT-Aa04 mature light chain variable domain protein sequence |
| 12 | SCT-Aa05 mature heavy chain variable domain protein sequence |
| 13 | SCT-Aa05 mature light chain variable domain protein sequence |
| 14 | SCT-Aa06 mature heavy chain variable domain protein sequence |
| 15 | SCT-Aa06 mature light chain variable domain protein sequence |
| 16 | SCT-Aa07 mature heavy chain variable domain protein sequence |
| 17 | SCT-Aa07 mature light chain variable domain protein sequence |
| 18 | SCT-Aa08 mature heavy chain variable domain protein sequence |
| 19 | SCT-Aa08 mature light chain variable domain protein sequence |
| 20 | SCT-Aa09 mature heavy chain variable domain protein sequence |
| 21 | SCT-Aa09 mature light chain variable domain protein sequence |
| 22 | SCT-Aa10 mature heavy chain variable domain protein sequence |
| 23 | SCT-Aa10 mature light chain variable domain protein sequence |
| 24 | SCT-Aa11 mature heavy chain variable domain protein sequence |

TABLE 1-continued

| SEQ ID NO. | Description of sequence |
|---|---|
| 25 | SCT-Aa11 mature light chain variable domain protein sequence |
| 26 | SCT-Aa12 mature heavy chain variable domain protein sequence |
| 27 | SCT-Aa12 mature light chain variable domain protein sequence |
| 28 | SCT-Aa13 mature heavy chain variable domain protein sequence |
| 29 | SCT-Aa14 mature heavy chain variable domain protein sequence |
| 30 | SCT-Aa14 mature light chain variable domain protein sequence |
| 31 | SCT-Aa15 mature heavy chain variable domain protein sequence |
| 32 | SCT-Aa15 mature light chain variable domain protein sequence |
| 33 | SCT-Aa16 mature heavy chain variable domain protein sequence |
| 34 | SCT-Aa16 mature light chain variable domain protein sequence |
| 35 | SCT-Aa17 mature heavy chain variable domain protein sequence |
| 36 | SCT-Aa17 mature light chain variable domain protein sequence |
| 37 | SCT-Aa18 mature heavy chain variable domain protein sequence |
| 38 | SCT-Aa18 mature light chain variable domain protein sequence |
| 39 | SCT-Aa19 mature heavy chain variable domain protein sequence |
| 40 | SCT-Aa19 mature light chain variable domain protein sequence |

DETAILED DESCRIPTION

Figure 1:
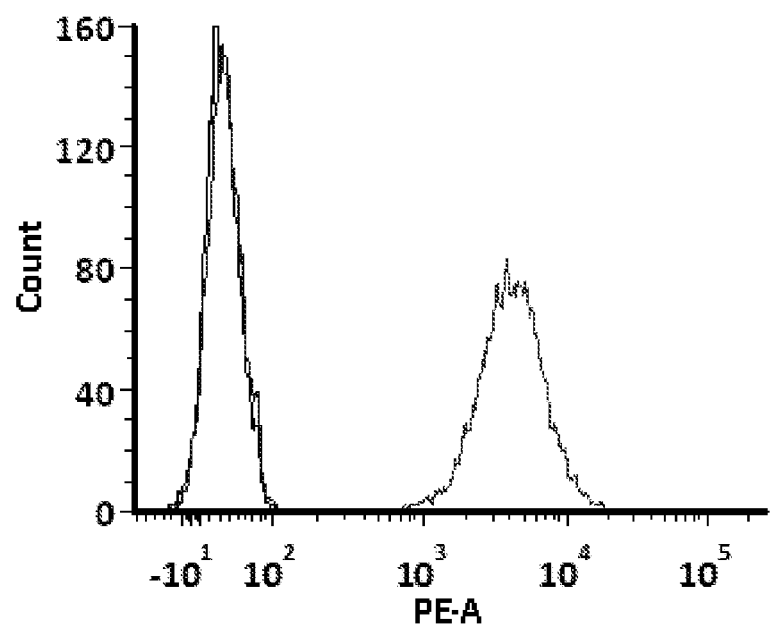
FIG. 1. shows a flow cytometry plot for anti-BCMA antibody SCT-Aa02 that depicts binding to 293T cells transfected with BCMA.

The disclosure provides antibodies that bind to BCMA and methods of use thereof. In one embodiment, the disclosure provides an isolated antibody that binds to SEQ ID NO:1.

Antibodies

The disclosure provides antibodies that bind specifically to SEQ ID NO:1. The term "antibody" as used herein, includes both full-length immunoglobulins and antibody fragments that bind to BCMA. The antibodies can be, e.g., a monoclonal, polyclonal, chimeric, humanized, or single chain antibody. As used herein, the terms "antigen binding fragment," "fragment," and "antibody fragment" are used interchangeably to refer to any fragment that comprises a portion of a full-length antibody, generally at least the antigen binding portion or the variable region thereof. Examples of antibody fragments include, but are not limited to, diabodies, single-chain antibody molecules, multispecific antibodies, Fab, Fab', F(ab')2, Fv or scFv.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

The terms "treating," "treatment," and the like, as used herein, mean ameliorating a disease, so as to reduce, ameliorate, or eliminate its cause, its progression, its severity, or one or more of its symptoms, or otherwise beneficially alter the disease in a subject. Reference to "treating," or "treatment" of a patient is intended to include prophylaxis. Treatment may also be preemptive in nature, i.e., it may include prevention of disease in a subject exposed to or at risk for the disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The terms "subject" and "patient" are used interchangeably herein to mean all mammals including humans. Examples of subjects include, but are not limited to, humans, monkeys, dogs, cats, horses, cows, goats, sheep, pigs, and rabbits. In one embodiment, the subject or patient is a human.

In some embodiments, the antibodies or antibody fragments of the present disclosure use BCMA to "target" B-cell lymphomas. In essence, such targeting can be generalized as follows: antibodies or antibody fragments of the present disclosure specific to the BCMA surface antigen of B-cells are, for example, injected into a subject and specifically bind to the BCMA cell surface antigen of both normal and malignant B-cells; this binding leads to the destruction and/or depletion of neoplastic B-cells. Additionally, chemical agents (e.g., chemotherapeutics) or radioactive labels (e.g., radiotherapeutics) having the potential to destroy cancer cells and/or tumors can be conjugated to the antibodies or antibody fragments of the present disclosure such that the agent is specifically "delivered" to the targeted B-cells, such as, for example, neoplastic B-cells. In some embodiments, the methods of the present disclosure comprise administering an antibody or antibody fragment that is not conjugated to a chemical agent or radioactive label. In some embodiments, the methods of the present disclosure comprise administering an antibody or antibody fragment that is not conjugated to a cytotoxic agent. For discovering and developing antibody therapeutics generally known in the art, please see U.S. Pat. No. 10,072,088, which is incorporated in its entirety by reference.

The provided antibodies may be used to diagnose, treat, or monitor BCMA-expressing cancer and its progression, regression, or stability; to determine whether or not a patient should be treated for cancer; or to determine whether or not a subject is afflicted with BCMA-expressing cancer and thus may be amenable to treatment with a BCMA-specific anti-cancer therapeutic. In some embodiments, the antibodies or fragments thereof described herein may be used for various in vitro molecular-biology applications such as, for example, enzyme-linked immunosorbent assays (ELISA), Western blots, immunohistochemistry, immunocytochemistry, flow cytometry and fluorescence-activated cell sorting (FACS), immunoprecipitation, and/or enzyme-linked immunospotting. In some embodiments, the antibodies or fragments thereof may be packaged in kits with or without additional reagents known to those of skill in the art for practicing any of the molecular biology techniques disclosed above.

The disclosure provides the antibodies SCT-Aa01, SCT-Aa02, SCT-Aa03, SCT-Aa04, SCT-Aa05, SCT-Aa06, SCT-Aa07, SCT-Aa08, SCT-Aa09, SCT-Aa10, SCT-Aa11, SCT-Aa12, SCT-Aa13, SCT-Aa14, SCT-Aa15, SCT-Aa16, SCT-Aa17, SCT-Aa18, and SCT-Aa19. Each of these is a murine monoclonal antibody.

Additionally, recombinant anti-BCMA antibodies, such as chimeric and humanized monoclonal antibodies, comprising both human and non-human portions, which can be made using standard recombinant DNA techniques, are within the scope of the disclosure. Such chimeric and humanized monoclonal antibodies can be produced by recombinant DNA techniques such as, for example, the methods described in U.S. Pat. No. 7,112,421; Better et al. (1988) Science 240:1041-1043; or Liu et al. (1987) Proc. Natl. Acad. Sci. USA 84:3439-3443.

Antibody Variable Domain Sequence

The antibodies of the disclosure may comprise the heavy chain variable domain sequences of SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:31, SEQ ID NO:33, SEQ ID NO:35, SEQ ID NO:37, or SEQ ID NO:39. The heavy chain variable domain sequences may consist essentially of SEQ ID NO:4, SEQ ID NO:6, SEQ ID NO:8, or SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:31, SEQ ID NO:33, SEQ ID NO:35, SEQ ID NO:37, or SEQ ID NO:39.

The antibodies of the disclosure may comprise the light chain variable domain sequences of SEQ ID NO:5, SEQ ID NO:7, SEQ ID NO:9, SEQ ID NO:11 SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:19, SEQ ID NO:30, SEQ ID NO:32, SEQ ID NO:34, SEQ ID NO:36, SEQ ID NO:38, or SEQ ID NO:40. The light chain variable domain sequences may consist essentially of SEQ ID NO:5, SEQ ID NO:7, SEQ ID NO:9, or SEQ ID NO:11 SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:19, SEQ ID NO:30, SEQ ID NO:32, SEQ ID NO:34, SEQ ID NO:36, SEQ ID NO:38, or SEQ ID NO:40.

The disclosure also provides a variable domain sequence comprising a sequence that is at least 80%, at least 85%, at least 90%, or at least 95% identical to a sequence selected from SEQ ID NO:4, SEQ ID NO:6, SEQ ID NO:8, or SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:29, SEQ ID NO:31, SEQ ID NO:33, SEQ ID NO:35, SEQ ID NO:37, and SEQ ID NO:39. The disclosure also provides a variable domain sequence comprising a sequence that is at least 80%, at least 85%, at least 90%, or at least 95% identical to a sequence selected from SEQ ID NO:5, SEQ ID NO:7, SEQ ID NO:9, or SEQ ID NO:11 SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:30, SEQ ID NO:32, SEQ ID NO:34, SEQ ID NO:36, SEQ ID NO:38, and SEQ ID NO:40. The disclosure also provides antibodies comprising a heavy chain variable domain sequence that is at least 80%, at least 85%, at least 90%, or at least 95% identical to SEQ ID NO:4 and a light chain variable domain sequence that is at least 80%, at least 85%, at least 90%, or at least 95% identical to SEQ ID NO:5. The disclosure includes antibodies comprising a heavy chain variable domain sequence that is at least 80%, at least 85%, at least 90%, or at least 95% identical to SEQ ID NO:6 and a light chain variable domain sequence that is at least 80%, at least 85%, at least 90%, or at least 95% identical to SEQ ID NO:7. The disclosure includes antibodies comprising a heavy chain variable domain sequence that is at least 80%, at least 85%, at least 90%, or at least 95% identical to SEQ ID NO:8 and a light chain variable domain sequence that is at least 80%, at least 85%, at least 90%, or at least 95% identical to SEQ ID NO:9. The disclosure includes antibodies comprising a heavy chain variable domain sequence that is at least 80%, at least 85%, at least 90%, or at least 95% identical to SEQ ID NO:10 and a light chain variable domain sequence that is at least 80%, at least 85%, at least 90%, or at least 95% identical to SEQ ID NO:11. The disclosure includes antibodies comprising a heavy chain variable domain sequence that is at least 80%, at least 85%, at least 90%, or at least 95% identical to SEQ ID NO:12 and a light chain variable domain sequence that is at least 80%, at least 85%, at least 90%, or at least 95% identical to SEQ ID NO:13. The disclosure includes antibodies comprising a heavy chain variable domain sequence that is at least 80%, at least 85%, at least 90%, or at least 95% identical to SEQ ID NO:14 and a light chain variable domain sequence that is at least 80%, at least 85%, at least 90%, or at least 95% identical to SEQ ID NO:15. The disclosure includes antibodies comprising a heavy chain variable domain sequence that is at least 80%, at least 85%, at least 90%, or at least 95% identical to SEQ ID NO:16 and a light chain variable domain sequence that is at least 80%, at least 85%, at least 90%, or at least 95% identical to SEQ ID NO:17. The disclosure includes antibodies comprising a heavy chain variable domain sequence that is at least 80%, at least 85%, at least 90%, or at least 95% identical to SEQ ID NO:18 and a light chain variable domain sequence that is at least 80%, at least 85%, at least 90%, or at least 95% identical to SEQ ID NO:19. The disclosure includes antibodies comprising a heavy chain variable domain sequence that is at least 80%, at least 85%, at least 90%, or at least 95% identical to SEQ ID NO:20 and a light chain variable domain sequence that is at least 80%, at least 85%, at least 90%, or at least 95% identical to SEQ ID NO:21. The disclosure includes antibodies comprising a heavy chain variable domain sequence that is at least 80%, at least 85%, at least 90%, or at least 95% identical to SEQ ID NO:22 and a light chain variable domain sequence that is at least 80%, at least 85%, at least 90%, or at least 95% identical to SEQ ID NO:23. The disclosure includes antibodies comprising a heavy chain variable domain sequence that is at least 80%, at least 85%, at least 90%, or at least 95% identical to SEQ ID NO:24 and a light chain variable domain sequence that is at least 80%, at least 85%, at least 90%, or at least 95% identical to SEQ ID NO:25. The disclosure includes antibodies comprising a heavy chain variable domain sequence that is at least 80%, at least 85%, at least 90%, or at least 95% identical to SEQ ID NO:26 and a light chain variable domain sequence that is at least 80%, at least 85%, at least 90%, or at least 95% identical to SEQ ID NO:27. The disclosure includes antibodies comprising a heavy chain variable domain sequence that is at least 80%, at least 85%, at least 90%, or at least 95% identical to SEQ ID NO:28 and a light chain variable domain sequence that is at least 80%, at least 85%, at least 90%, or at least 95% identical to SEQ ID NO:19. The disclosure includes antibodies comprising a heavy chain variable domain sequence that is at least 80%, at least 85%, at least 90%, or at least 95% identical to SEQ ID NO:29 and a light chain variable domain sequence that is at least 80%, at least 85%, at least 90%, or at least 95% identical to SEQ ID NO:30. The disclosure includes antibodies comprising a heavy chain variable domain sequence that is at least 80%, at least 85%, at least 90%, or at least 95% identical to SEQ ID NO:31 and a light chain variable domain sequence that is at least 80%, at least 85%, at least 90%, or at least 95% identical to SEQ ID NO:32. The disclosure includes antibodies comprising a heavy chain variable domain sequence that is at least 80%, at least 85%, at least 90%, or at least 95% identical to SEQ ID NO:33 and a light chain variable domain sequence that is at least 80%, at least 85%, at least 90%, or at least 95% identical to SEQ ID NO:34. The disclosure includes antibodies comprising a heavy chain variable domain sequence that is at least 80%, at least 85%, at least 90%, or at least 95% identical to SEQ ID NO:35 and a light chain variable domain sequence that is at least 80%, at least 85%, at least 90%, or at least 95% identical to SEQ ID NO:36. The disclosure includes antibodies comprising a heavy chain variable domain sequence that is at least 80%, at least 85%, at least 90%, or at least 95% identical to SEQ ID NO:37 and a light chain variable domain sequence that is at least 80%, at least 85%, at least 90%, or at least 95% identical to SEQ ID NO:38. The disclosure includes antibodies comprising a heavy chain variable domain sequence that is at least 80%, at least 85%, at least 90%, or at least 95% identical to SEQ ID NO:39 and a light chain variable domain sequence that is at least 80%, at least 85%, at least 90%, or at least 95% identical to SEQ ID NO:40.

Table 1 provides a summary of the BCMA-specific antibodies described herein.

Pharmaceutical Compositions

Pharmaceutical compositions comprising the antibodies or antibody fragments of the present disclosure are also contemplated and can be used in the methods disclosed herein. Pharmaceutical compositions can comprise one or more of the antibodies or antibody fragments described herein and a pharmaceutically acceptable carrier or excipient. Although the carrier or excipient may facilitate administration, it should not itself induce the production of antibodies harmful to the subject or individual receiving the composition; nor should it be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles, and are known to one of skill in the art.

The antibodies or an antigen binding fragments described herein, or the pharmaceutical compositions disclosed herein, may be administered by any number of routes including, but not limited to, oral, intravenous, intramuscular, intra-arterial, intramedullary, intraperitoneal, intrathecal, intraventricular, transdermal, transcutaneous, topical, subcutaneous, intranasal, enteral, sublingual, intravaginal or rectal routes. Typically, the therapeutic compositions may be prepared as injectables, either as liquid solutions or suspensions. Solid forms suitable for solution in, or suspension in, liquid vehicles prior to injection may also be prepared.

In one embodiment, the antibody, or an antigen binding fragment thereof, or pharmaceutical composition is administered intravenously. In another embodiment, the antibody, or an antigen binding fragment thereof, or pharmaceutical composition is administered by intravenous infusion.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule. Known antibody-based pharmaceuticals provide guidance relating to frequency of administration e.g., whether a pharmaceutical should be delivered daily, weekly, monthly, etc. Frequency and dosage may also depend on the severity of symptoms.

It will be appreciated that the active ingredient in the composition will be an antibody molecule, an antibody fragment or variants and derivatives thereof. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

The methods of the present invention can use an antibody, or an antigen binding fragment thereof, as described above, alone or in combination with other pharmaceutically active compounds, to treat conditions such as those disclosed hereinabove. The additional pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of an antibody, or an antigen binding fragment thereof, of the present invention and one or more additional pharmaceutically active compounds.

In some embodiments, the antibody, or an antigen binding fragment thereof, of the present invention is used in combination with existing BCMA-related disease therapies.

EXAMPLES

The following example is put forth so as to provide those of ordinary skill in the art with a complete description of how to make and use the present disclosure and is not intended to limit the scope of present disclosure nor is it intended to represent that the experiment below is all or the only experiment that could be performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Identification of a Murine Anti-Human BCMA Antibody Immunization & Single Cell Suspension Generation Recombinant human BCMA (huBCMA-His, Catalog No.: BCA-H522y, ACROBiosystems, Beijing, China, SEQ ID NO:2) was used to immunize young C57/BL6 mice each with 80 µg huBCMA-His in Sigma Adjuvant System® (Sigma-Aldrich, St. Louis, Mo.) using a rapid immunization protocol of Antibody Solutions (Sunnyvale, Calif.). The lymph nodes were harvested along with serum on day 35. Single cell suspension of the lymph node was generated, and the suspension was filtered through a 70 µm mesh (BD Bioscience) to remove clumps.

Plasma Cell Isolation, Antibody Capture, and Antigen Interrogation

The filtered lymphocyte suspension was enriched for plasma cells actively secreting IgGs instead of using a kit based on cell surface expression of CD138 (Miltenyi, Auburn, Calif.). Afterwards, freshly enriched plasma cells were spread on a PDMS device to allow a single cell deposition in the microwells on the device. Antibody secreted from each ASC was captured on a derivatized microscope slide (U.S. Pat. No. 9,328,172). Antigen-specific antibody secreting cells were identified by interrogating the antibody capture slide with varying concentrations of fluorescently labeled BCMA-huFC (ACROBiosystems, Beijing, China, Catalog No.: BC7-H5254, SEQ ID NO:3).

mRNA Capture

After antibody capture, the medium was removed, and replaced with lysis buffer followed by prompt closure of the top of the microwells with a custom oligonucleotide microarray on a microscope slide (Agilent, Santa Clara, Calif.). This procedure was previously described in U.S. Pat. No. 9,328,172. The custom oligonucleotide microarray is prepared such that each feature contains not only a unique tag specifying its coordinate but also capture probes for all subclasses (1, 2a, 2b, and 3) of murine IgG heavy chain, murine Ig kappa light chain. Hybridization was allowed to proceed overnight.

cDNA Synthesis, PCR Amplification, and Next Generation Sequencing

Captured mRNA on the custom microarray was further processed to synthesize cDNA of each mRNA incorporating the unique tag originally on each feature. The cDNA is then amplify using a Taq polymerase (Promega, Madison, Wis.) and appropriate set of primers to allow amplification of the following genes: variable domain of IgG heavy chain subclasses and variable domain of Ig kappa light chain. Though now released from cells, these fragments of each gene are now labeled with the unique tag from the custom oligonucleotide microarray manifesting their originating locations. The amplicons were further manipulated to have appropriate sequence attached at both ends to enable sequencing on an Illumina MiSeq instrument using 2×250 bp chemistry at SeqMatic LLC (Fremont, Calif.).

Bioinformatic Analysis of Images and DNA Sequences

Sequencing reads from MiSeq were processed and the embedded tag in each read was identified and converted into coordinates. The coordinates were plotted to yield a synthetic map of the mRNA recovered. Most of the coordinates form clusters that designate the location of the originating cell for the recovered mRNA sequences. Next, a complementarity-determining region 3 (CDR3) motif present in each read with the coordinates was identified and collated according to the clusters that matched the location of an antibody spot visualized by an appropriate fluorescently labeled secondary antibody. Identical or nearly identical CDR3s for a given antibody spot were organized and form consistent pair of $V_H$ and $V_L$ sequences. The remaining part of sequences containing the identified CDR3s were identified and assembled into full-length cDNA sequences for $V_H$ and $V_L$. The pair of full-length cDNA was correlated with the affinity measurements associated with each of the antigen-specific antibody spot.

Example 2: Molecular Reconstruction and Recombinant Expression of Anti-BCMA Antibodies The paired $V_H$ and $V_L$ anti-BCMA antibody sequences were used to synthesize corresponding gene fragments by a service provider according to the known art. The resulting gene fragments were each cloned into an appropriate plasmid vector with either mouse IgG1 heavy chain constant region and mouse kappa light chain constant region or human IgG1 heavy chain constant region and human kappa light chain and the appropriate H and L chain pair was transfected into an appropriate mammalian host, such as HEK293, for recombinant expression to produce an antibody preparation in full-IgG format. The antibody preparations were characterized by measurements at OD280 to assess the amount produced and by gel electrophoresis on PAGE to assess the size of the antibody chains produced. A subset of the anti-human BCMA antibodies of the present disclosure was reconstructed and recombinantly expressed. Their respective clone preparation IDs are shown in Table 2.

TABLE 2

| mAb aa ID | Heavy chain constant region | Light chain constant region | Clone preparation ID |
|---|---|---|---|
| SCT-Aa01 | Mouse IgG1 | Mouse kappa | SCT-Aa01(m/m) |
| SCT-Aa02 | Mouse IgG1 | Mouse kappa | SCT-Aa02(m/m) |
| SCT-Aa03 | Mouse IgG1 | Mouse kappa | SCT-Aa03(m/m) |
| SCT-Aa04 | Mouse IgG1 | Mouse kappa | SCT-Aa04(m/m) |
| SCT-Aa05 | Mouse IgG1 | Mouse kappa | SCT-Aa05(m/m) |
| SCT-Aa06 | Mouse IgG1 | Mouse kappa | SCT-Aa06(m/m) |
| SCT-Aa08 | Mouse IgG1 | Mouse kappa | SCT-Aa08(m/m) |
| SCT-Aa09 | Mouse IgG1 | Mouse kappa | SCT-Aa09(m/m) |
| SCT-Aa10 | Mouse IgG1 | Mouse kappa | SCT-Aa10(m/m) |
| SCT-Aa11 | Mouse IgG1 | Mouse kappa | SCT-Aa11(m/m) |
| SCT-Aa12 | Mouse IgG1 | Mouse kappa | SCT-Aa12(m/m) |
| SCT-Aa13 | Mouse IgG1 | Mouse kappa | SCT-Aa13(m/m) |
| SCT-Aa14 | Mouse IgG1 | Mouse kappa | SCT-Aa14(m/m) |
| SCT-Aa15 | Mouse IgG1 | Mouse kappa | SCT-Aa15(m/m) |
| SCT-Aa01 | Human IgG1 | Human kappa | SCT-Aa01(h/h) |
| SCT-Aa02 | Human IgG1 | Human kappa | SCT-Aa02(h/h) |
| SCT-Aa03 | Human IgG1 | Human kappa | SCT-Aa03(h/h) |
| SCT-Aa04 | Human IgG1 | Human kappa | SCT-Aa04(h/h) |
| SCT-Aa05 | Human IgG1 | Human kappa | SCT-Aa05(h/h) |
| SCT-Aa06 | Human IgG1 | Human kappa | SCT-Aa06(h/h) |
| SCT-Aa08 | Human IgG1 | Human kappa | SCT-Aa08(h/h) |
| SCT-Aa10 | Human IgG1 | Human kappa | SCT-Aa10(h/h) |
| SCT-Aa11 | Human IgG1 | Human kappa | SCT-Aa11(h/h) |
| SCT-Aa13 | Human IgG1 | Human kappa | SCT-Aa13(h/h) |
| SCT-Aa15 | Human IgG1 | Human kappa | SCT-Aa15(h/h) |
| SCT-Aa16 | Human IgG1 | Human kappa | SCT-Aa16(h/h) |
| SCT-Aa17 | Human IgG1 | Human kappa | SCT-Aa17(h/h) |
| SCT-Aa18 | Human IgG1 | Human kappa | SCT-Aa18(h/h) |
| SCT-Aa19 | Human IgG1 | Human kappa | SCT-Aa19(h/h) |

Example 3: Characterization of the Recombinant Anti-Human BCMA Antibodies by ELISA The recombinantly expressed antibodies were used to assess binding activity to BCMA of different species origins by conventional ELISA according to the known art. Recombinant human BCMA, cyno BCMA, and mouse BCMA were coated onto ELISA plates to detect binding at serially diluted concentrations of the anti-BCMA antibody preparations.

The ability for antibodies of the present disclosure to bind human BCMA was measured with an ELISA assay. For the BCMA binding assay, a 96-well plate (Nunc) is coated with human BCMA with a His tag (ACROBiosystems, Catalog No.: AC108P1-180611F2-Bulk, SEQ ID NO:2) at 0.2 μg/well overnight at 4° C. Wells are blocked for 2 h with blocking buffer (PBS containing 3% bovine serum albumin). Wells are washed three times with PBS containing 0.1% Tween-20. Anti-human BCMA antibodies of the present disclosure or control IgG (100 μL) is then added and incubated at room temperature for 1 h. After washing, the plate is incubated with 100 μL of goat anti-mouse IgG Fcγ Fragment Specific-HRP conjugate (Jackson ImmunoResearch) at room temperature for 1 h. The plates are washed and then incubated with 100 μL of 3,3′,5,5′-tetra-methylbenzidine. The absorbance at 450 nm is read on a microplate reader. The half maximal effective concentration (EC50) is calculated using GraphPad Prism 6 software.

In experiments performed essentially as described above, anti-human BCMA antibodies of the present disclosure bind human BCMA with a His tag (ACROBiosystems, Beijing, China, Catalog No.: BCA-H522y, SEQ ID NO:2) with an EC50 values shown in Table 3.

TABLE 3

| Clone preparation ID | EC50 (μg/mL) |
|---|---|
| SCT-Aa01(m/m) | 0.00292 |
| SCT-Aa02(m/m) | 0.00286 |
| SCT-Aa03(m/m) | 0.00171 |
| SCT-Aa04(m/m) | 0.00232 |
| SCT-Aa05(m/m) | 0.00212 |
| SCT-Aa06(m/m) | 0.00234 |
| SCT-Aa08(m/m) | 0.00246 |
| SCT-Aa09(m/m) | 0.00196 |
| SCT-Aa10(m/m) | 0.00257 |
| SCT-Aa11(m/m) | 0.00238 |
| SCT-Aa12(m/m) | 0.00170 |
| SCT-Aa13(m/m) | 0.00264 |
| SCT-Aa14(m/m) | 0.00252 |
| SCT-Aa01(h/h) | 0.00338 |
| SCT-Aa02(h/h) | 0.00285 |
| SCT-Aa03(h/h) | 0.00346 |
| SCT-Aa04(h/h) | 0.00248 |
| SCT-Aa05(h/h) | 0.00235 |
| SCT-Aa06(h/h) | 0.00278 |
| SCT-Aa08(h/h) | 0.00374 |
| SCT-Aa10(h/h) | 0.00286 |
| SCT-Aa11(h/h) | 0.00385 |
| SCT-Aa13(h/h) | 0.00268 |
| SCT-Aa15(h/h) | 0.00371 |
| SCT-Aa16(h/h) | 0.00201 |
| SCT-Aa17(h/h) | 0.00356 |
| SCT-Aa18(h/h) | 0.00268 |
| SCT-Aa19(h/h) | 0.00338 |

In experiments performed essentially as described above, anti-human BCMA antibodies of the present disclosure bind cyno BCMA with a His tag (ACROBiosystems, Beijing, China, Catalog No.: BCA-052H7, SEQ ID NO:110) with an EC50 values shown in Table 4.

TABLE 4

| Clone preparation ID | EC50 (μg/mL) |
|---|---|
| SCT-Aa01(m/m) | 0.00570 |
| SCT-Aa02(m/m) | 0.08909 |
| SCT-Aa03(m/m) | Weak positive |
| SCT-Aa04(m/m) | 2.04534 |
| SCT-Aa05(m/m) | Weak positive |
| SCT-Aa06(m/m) | Weak positive |
| SCT-Aa08(m/m) | Weak positive |
| SCT-Aa09(m/m) | 5.56536 |
| SCT-Aa10(m/m) | Weak positive |
| SCT-Aa11(m/m) | Weak positive |
| SCT-Aa12(m/m) | 9.74196 |
| SCT-Aa13(m/m) | 0.17426 |
| SCT-Aa14(m/m) | Weak positive |
| SCT-Aa01(h/h) | Strong positive |
| SCT-Aa02(h/h) | 0.04327 |
| SCT-Aa03(h/h) | 1.59537 |
| SCT-Aa04(h/h) | Weak positive |
| SCT-Aa05(h/h) | Weak positive |
| SCT-Aa06(h/h) | 0.09763 |
| SCT-Aa08(h/h) | Weak positive |

TABLE 4-continued

| Clone preparation ID | EC50 (μg/mL) |
|---|---|
| SCT-Aa10(h/h) | Weak positive |
| SCT-Aa11(h/h) | Weak positive |
| SCT-Aa13(h/h) | 0.13064 |
| SCT-Aa15(h/h) | Weak positive |
| SCT-Aa16(h/h) | 0.07782 |
| SCT-Aa17(h/h) | 2.17308 |
| SCT-Aa18(h/h) | 0.07882 |
| SCT-Aa19(h/h) | Weak positive |

In experiments performed essentially as described above, anti-human BCMA antibodies of the present disclosure bind mouse BCMA with a His tag (ACROBiosystems, Beijing, China, Catalog No.: BCA-M52H3, SEQ ID NO:109) with an EC50 values shown in Table 5.

TABLE 5

| Clone preparation ID | EC50 (μg/mL) |
|---|---|
| SCT-Aa01(m/m) | Weak positive |
| SCT-Aa02(m/m) | 0.00262 |
| SCT-Aa03(m/m) | 0.07913 |
| SCT-Aa04(m/m) | 0.03428 |
| SCT-Aa05(m/m) | 0.05222 |
| SCT-Aa06(m/m) | Weak positive |
| SCT-Aa08(m/m) | 0.68189 |
| SCT-Aa09(m/m) | Weak positive |
| SCT-Aa10(m/m) | 8.03235 |
| SCT-Aa11(m/m) | 3.89800 |
| SCT-Aa12(m/m) | 0.01066 |
| SCT-Aa13(m/m) | 0.52875 |
| SCT-Aa14(m/m) | 2.33720 |
| SCT-Aa01(h/h) | Weak positive |
| SCT-Aa02(h/h) | Strong positive |
| SCT-Aa03(h/h) | 0.01081 |
| SCT-Aa04(h/h) | 0.27034 |
| SCT-Aa05(h/h) | 0.02945 |
| SCT-Aa06(h/h) | 0.09718 |
| SCT-Aa08(h/h) | 0.37743 |
| SCT-Aa10(h/h) | 0.94096 |
| SCT-Aa11(h/h) | Weak positive |
| SCT-Aa13(h/h) | 0.01902 |
| SCT-Aa15(h/h) | 0.22620 |
| SCT-Aa16(h/h) | 1.08481 |
| SCT-Aa17(h/h) | 4.33462 |
| SCT-Aa18(h/h) | 0.27113 |
| SCT-Aa19(h/h) | Weak positive |

Example 4: Characterization of the Recombinant Anti-Human BCMA Antibodies by Surface Plasmon Resonance The binding affinity of select anti-BCMA was measured on a surface plasmon resonance (SPR) instrument, Biacore T200™, against human BCMA by a method known in the art.

In experiments performed essentially as described above, a subset of anti-human BCMA antibodies of the present disclosure bind human BCMA with a His tag (ACROBiosystems, Beijing, China, Catalog No.: BCA-H522y, SEQ ID NO:2) with affinity shown in Table 6.

TABLE 6

| Clone preparation ID | $K_a$ (1/Ms) | $K_d$ (1/s) | $K_D$ (RU) | $R_{max}$ (RU) |
|---|---|---|---|---|
| SCT-Aa01(m/m) | 2.55E+05 | 1.75E−02 | 6.86E−08 | 36.22 |
| SCT-Aa02(m/m) | 2.92E+05 | 1.13E−04 | 3.88E−10 | 29.18 |
| SCT-Aa03(m/m) | 2.24E+05 | 2.63E−03 | 1.17E−08 | 39.07 |
| SCT-Aa04(m/m) | 2.25E+06 | 1.26E−02 | 5.62E−09 | 35.41 |

TABLE 6-continued

| Clone preparation ID | $K_a$ (1/Ms) | $K_d$ (1/s) | $K_D$ (RU) | $R_{max}$ (RU) |
|---|---|---|---|---|
| SCT-Aa05(m/m) | 6.92E+04 | 3.40E-04 | 4.91E-09 | 33.85 |
| SCT-Aa06(m/m) | 3.15E+06 | 1.63E-02 | 5.16E-09 | 37.70 |
| SCT-Aa08(m/m) | 3.36E+06 | 5.27E-02 | 1.57E-08 | 29.71 |
| SCT-Aa09(m/m) | 1.66E+06 | 1.27E-01 | 7.66E-08 | 32.31 |
| SCT-Aa10(m/m) | 2.34E+06 | 2.24E-02 | 9.56E-09 | 32.90 |
| SCT-Aa11(m/m) | 2.25E+06 | 9.45E-02 | 4.20E-08 | 27.53 |
| SCT-Aa12(m/m) | 2.20E+06 | 1.10E-02 | 5.01E-09 | 36.92 |
| SCT-Aa13(m/m) | 8.17E+05 | 3.58E-02 | 4.38E-08 | 34.74 |
| SCT-Aa14(m/m) | 1.85E+06 | 3.76E-02 | 2.04E-08 | 29.48 |
| SCT-Aa01(h/h) | 8.19E+05 | 3.55E-02 | 4.34E-08 | 26.73 |
| SCT-Aa02(h/h) | 3.06E+05 | 3.74E-04 | 1.22E-09 | 36.67 |
| SCT-Aa03(h/h) | 2.99E+05 | 2.84E-03 | 9.49E-09 | 39.23 |
| SCT-Aa04(h/h) | 1.04E+06 | 3.40E-02 | 3.26E-08 | 44.15 |
| SCT-Aa05(h/h) | 1.00E+05 | 9.95E-04 | 9.93E-09 | 44.81 |
| SCT-Aa06(h/h) | 3.72E+06 | 2.00E-02 | 5.38E-09 | 46.92 |
| SCT-Aa08(h/h) | 3.36E+06 | 5.92E-02 | 1.76E-08 | 48.19 |
| SCT-Aa10(h/h) | 3.10E+06 | 2.84E-02 | 9.17E-09 | 44.18 |
| SCT-Aa11(h/h) | 2.40E+06 | 1.13E-01 | 4.71E-08 | 42.97 |
| SCT-Aa13(h/h) | 3.23E+06 | 1.57E-02 | 4.85E-09 | 43.72 |
| SCT-Aa15(h/h) | 5.21E+06 | 6.20E-03 | 1.19E-09 | 45.2 |
| SCT-Aa16(h/h) | 7.43E+06 | 1.99E-01 | 2.67E-08 | 45.53 |
| SCT-Aa17(h/h) | 5.39E+06 | 1.32E-02 | 2.45E-09 | 32.73 |
| SCT-Aa18(h/h) | 4.15E+06 | 5.06E-02 | 1.22E-08 | 35.91 |
| SCT-Aa19(h/h) | 5.21E+06 | 6.20E-03 | 1.19E-09 | 45.20 |

Example 5: Characterization of the Recombinant Anti-Human BCMA Antibodies by Flow Cytometry A subset of anti-human BCMA antibodies of the present disclosure were assayed for binding to 293T cells transfected with BCMA and the flow cytometry plot for one of the antibodies (SCT-Aa02) is shown in FIG. 1.

A subset of anti-human BCMA antibodies of the present disclosure were assayed for binding to 293T cells transfected with BCMA and the fraction of cells bound the labeled antibody above background defined by control with parental 293T cells is shown in Table 7.

TABLE 7

| Clone preparation ID | Positive (%) |
|---|---|
| SCT-Aa01(m/m) | 48.2 |
| SCT-Aa02(m/m) | 96.3 |
| SCT-Aa03(m/m) | 91.6 |
| SCT-Aa04(m/m) | 88.9 |
| SCT-Aa05(m/m) | 94.3 |
| SCT-Aa06(m/m) | 91.6 |
| SCT-Aa08(m/m) | 70.6 |
| SCT-Aa09(m/m) | 16.9 |
| SCT-Aa10(m/m) | 82.9 |
| SCT-Aa11(m/m) | 34.6 |
| SCT-Aa12(m/m) | 85.7 |
| SCT-Aa13(m/m) | 84.4 |
| SCT-Aa14(m/m) | 52.2 |
| SCT-Aa01(h/h) | 12.3 |
| SCT-Aa02(h/h) | 81.9 |
| SCT-Aa03(h/h) | 75.1 |
| SCT-Aa04(h/h) | 72.0 |
| SCT-Aa05(h/h) | 76.3 |
| SCT-Aa06(h/h) | 82.8 |
| SCT-Aa08(h/h) | 57.5 |
| SCT-Aa10(h/h) | 57.9 |
| SCT-Aa11(h/h) | 34.9 |
| SCT-Aa13(h/h) | 74.3 |
| SCT-Aa15(h/h) | 32.0 |
| SCT-Aa16(h/h) | 68.1 |
| SCT-Aa17(h/h) | 43.0 |
| SCT-Aa18(h/h) | 76.1 |
| SCT-Aa19(h/h) | 51.0 |

A cell line expressing BCMA, H929, was used to assess binding by anti-BCMA antibodies on the native protein on the cell surface by flow cytometry according to the known art. A subset of anti-human BCMA antibodies were assayed for binding to H929 and the fraction of cells bound the labeled antibody above background defined by control is shown in Table 8.

TABLE 8

| Clone preparation ID | Positive (%) | Mean fluorescent intensity |
|---|---|---|
| SCT-Aa01(m/m) | 99.8 | 2087 |
| SCT-Aa02(m/m) | 100.0 | 4559 |
| SCT-Aa03(m/m) | 99.9 | 3918 |
| SCT-Aa04(m/m) | 99.9 | 3791 |
| SCT-Aa05(m/m) | 99.9 | 2015 |
| SCT-Aa06(m/m) | 99.9 | 4302 |
| SCT-Aa08(m/m) | 99.9 | 1819 |
| SCT-Aa09(m/m) | 18.4 | 102 |
| SCT-Aa10(m/m) | 99.9 | 2958 |
| SCT-Aa11(m/m) | 99.9 | 1519 |
| SCT-Aa12(m/m) | 99.9 | 3476 |
| SCT-Aa13(m/m) | 99.9 | 2565 |
| SCT-Aa14(m/m) | 75.1 | 475 |
| SCT-Aa01(h/h) | 55.2 | 411 |
| SCT-Aa02(h/h) | 99.2 | 1281 |
| SCT-Aa03(h/h) | 98.2 | 1069 |
| SCT-Aa04(h/h) | 96.5 | 623 |
| SCT-Aa05(h/h) | 96.5 | 758 |
| SCT-Aa06(h/h) | 99.6 | 1262 |
| SCT-Aa08(h/h) | 92.5 | 454 |
| SCT-Aa10(h/h) | 85.5 | 495 |
| SCT-Aa11(h/h) | 53.7 | 179 |
| SCT-Aa13(h/h) | 96.5 | 756 |
| SCT-Aa15(h/h) | 34.8 | 141 |
| SCT-Aa16(h/h) | 96.1 | 853 |
| SCT-Aa17(h/h) | 75.0 | 232 |
| SCT-Aa18(h/h) | 97.0 | 875 |
| SCT-Aa19(h/h) | 85.1 | 351 |

Figure 2A:
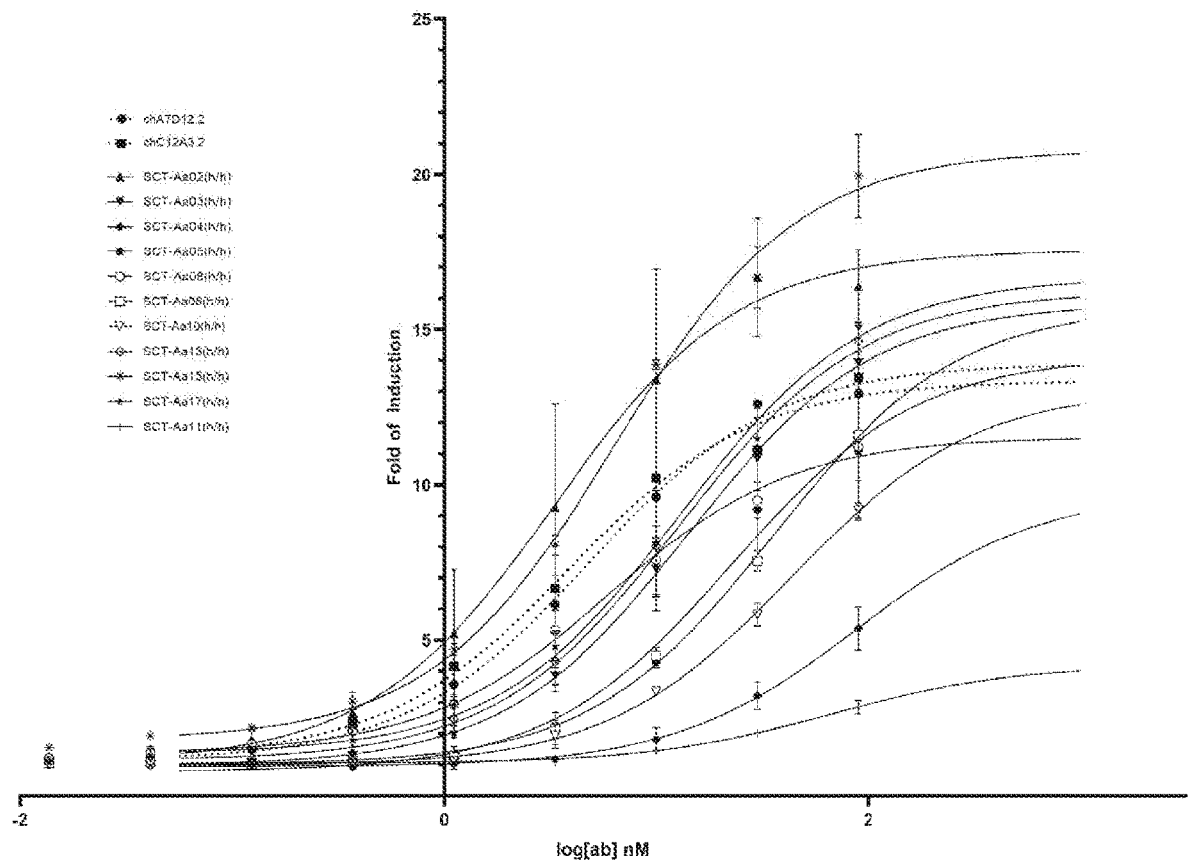
FIG. 2A. shows an antibody-dependent cellular cytotoxicity (ADCC) activity plot of a subset of anti-BCMA antibodies tested against a target cell-line (MM.1S) expressing BCMA.
Figure 2B:
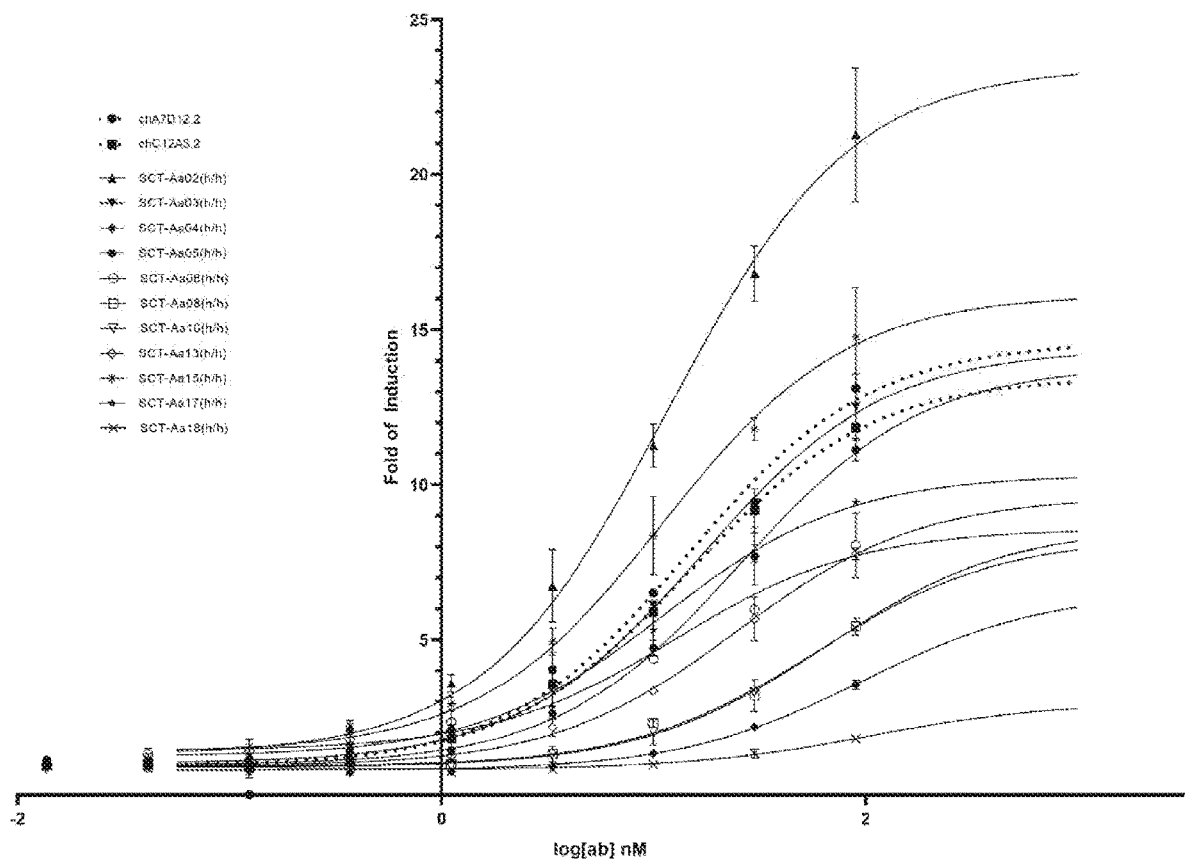
FIG. 2B. shows an ADCC activity plot of a subset of anti-BCMA antibodies tested against a target cell-line (U266) expressing BCMA.

Example 6: Characterization of the Recombinant Anti-Human BCMA Antibodies by Reporter Cell-Based Antibody-Dependent Cellular Cytotoxicity (ADCC) Assay In addition, ADCC activity of a subset of anti-BCMA antibodies was assessed using an engineered surrogate effector cell line, kit reagents, and a luminometer (Promega, Madison, Wis.) on 2 cell lines expressing BCMA, MM.1S and U266, as target cells and the results were used to compare against two benchmark antibodies (chA7D12.2 and chC12A3.2) from U.S. Pat. No. 9,034,324 with known ADCC activity (FIG. 2). The calculated EC50s for two target cell lines, MM.1S and U266, are listed in Table 9 and Table 10, respectively.

TABLE 9

| Clone preparation ID | EC50 for MM.1S |
|---|---|
| chAD7D12.2 | 4.87 |
| chC12A3.2 | 3.87 |
| SCT-Aa01(h/h) | Not determined |
| SCT-Aa02(h/h) | 3.29 |
| SCT-Aa03(h/h) | 14.12 |
| SCT-Aa04(h/h) | 89.21 |
| SCT-Aa05(h/h) | 22.92 |
| SCT-Aa06(h/h) | 5.97 |
| SCT-Aa08(h/h) | 35.80 |
| SCT-Aa10(h/h) | 43.34 |
| SCT-Aa11(h/h) | 67.23 |
| SCT-Aa13(h/h) | 12.86 |

TABLE 9-continued

| Clone preparation ID | EC50 for MM.1S |
|---|---|
| SCT-Aa15(h/h) | Not determined |
| SCT-Aa16(h/h) | 6.40 |
| SCT-Aa17(h/h) | Not determined |
| SCT-Aa18(h/h) | 12.92 |
| SCT-Aa19(h/h) | Not determined |

TABLE 10

| Clone preparation ID | EC50 for U266 |
|---|---|
| chAD7D12.2 | 14.55 |
| chC12A3.2 | 14.89 |
| SCT-Aa01(h/h) | Not determined |
| SCT-Aa02(h/h) | 11.69 |
| SCT-Aa03(h/h) | 16.79 |
| SCT-Aa04(h/h) | 97.41 |
| SCT-Aa05(h/h) | 25.40 |
| SCT-Aa06(h/h) | 12.56 |

TABLE 10-continued

| Clone preparation ID | EC50 for U266 |
|---|---|
| SCT-Aa08(h/h) | 58.66 |
| SCT-Aa10(h/h) | 64.26 |
| SCT-Aa11(h/h) | Not determined |
| SCT-Aa13(h/h) | 24.59 |
| SCT-Aa15(h/h) | Not determined |
| SCT-Aa16(h/h) | 11.10 |
| SCT-Aa17(h/h) | Not determined |
| SCT-Aa18(h/h) | 11.11 |
| SCT-Aa19(h/h) | 106.30 |

Some of the antibodies recovered from the antibody campaign described above are listed herein. The complementarity-determining region (CDR) sequences for the anti-BCMA antibodies heavy-chains (e.g., HCDR1) and light-chains (e.g., LCDR1) described herein are depicted in Table 11. The heavy-chain variable domain ($V_H$) and light-chain variable domain ($V_L$) sequences for the anti-BCMA antibodies described herein are depicted in Table 12.

TABLE 11

CDR sequences of mAbs generated against human BMCA
(SEQ ID NOs for each listed sequence are provided in parenthesis)

| mAb AA ID | HCDR1 | HCDR2 | HCDR3 | LCDR1 | LCDR2 | LCDR3 |
|---|---|---|---|---|---|---|
| SCT-Aa01 | GYSITSGYY (41) | IRYDGSN (65) | APYDYDYAMDF (87) | GNIHNY (54) | NAK (80) | QHFWSTPFT (99) |
| SCT-Aa02 | GIDFSRYW (50) | INPDSSTI (76) | ASLYYDYERDYAMDY (94) | QNVGTN (61) | SAS (85) | QQYHSYPFT (105) |
| SCT-Aa03 | GIDFSRYW (50) | INPDSSTI (76) | ASFYYDYDHAMDY (95) | QNVGTN (61) | SAS (85) | QQYNSYPFT (106) |
| SCT-Aa04 | GIDFSRYW (50) | INPDSSTI (76) | ASFYYDYDRGAAMDY (96) | QNVGTN (61) | SAS (85) | QQYNSYPYT (107) |
| SCT-Aa05 | GIDFSRYW (50) | INPDSSTI (76) | ASLYYDYEREYGMDY (97) | QNVGTN (61) | SAS (85) | QQYNSYPYT (107) |
| SCT-Aa06 | GYSFTGYF (51) | INPYNGDT (77) | ARLDYTNYNSYPMDY (98) | QGISNY (62) | YTS (86) | QQYSKFPWT (108) |
| SCT-Aa07 | GYSFTDHT (52) | IYPRDGST (69) | ARWDYEGFDC (88) | QRISDY (63) | YAS (81) | QNGHSFPPT (100) |
| SCT-Aa08 | GYTFIDHT (53) | IYPRIDSS (78) | ARWDYEGFDY (89) | QSISDY (55) | YAS (81) | QNGHSFPPT (100) |
| SCT-Aa09 | GYTFTDHT (42) | FYPRDDNT (79) | ARWDYEGFDY (89) | QSIRDY (64) | YAS (81) | QNGHSFPPT (100) |
| SCT-Aa10 | GYTFTDHT (42) | IFPRDGNT (66) | ARWDYEGFDC (88) | QSISDY (55) | YAS (81) | QNGHSFPPT (100) |
| SCT-Aa11 | GYTFTDHT (42) | IFPRDGTT (67) | ARWDYEGFDY (89) | QSISDY (55) | YAS (81) | QNGHSFPPT (100) |
| SCT-Aa12 | GYTFTDYT (43) | IFPSDGST (68) | ARWDYEGFDY (89) | QSISDY (55) | YAS (81) | QNGHSFPPT (100) |
| SCT-Aa13 | GYTFTDYT (43) | IYPRDGST (69) | ARWDYEGFDY (89) | QSISDY (55) | YAS (81) | QNGHSFPPT (100) |
| SCT-Aa14 | SYTFTDHT (44) | IFPRDGST (70) | ARWDYEGFDY (89) | QNISDY (56) | YAS (81) | QNGHSFPPT (100) |
| SCT-Aa15 | GSTFTDHT (45) | VYPRDGST (71) | ARWDYEGFDY (89) | QNISDY (56) | YAS (81) | QNGHSFPPT (100) |
| SCT-Aa16 | GYTFTNYI (46) | IIPYNDNT (72) | ATYEYDVGLDY (90) | QGIVNY (57) | NTS (82) | QQYSKLPWT (101) |

TABLE 11-continued

CDR sequences of mAbs generated against human BMCA
(SEQ ID NOs for each listed sequence are provided in parenthesis)

| mAb AA ID | HCDR1 | HCDR2 | HCDR3 | LCDR1 | LCDR2 | LCDR3 |
|---|---|---|---|---|---|---|
| SCT-Aa17 | GYTFTSYV (47) | INPYNDGT (73) | ARSDYDYGYAMDY (91) | ENIYSN (58) | SAT (83) | QHFWGPPWT (102) |
| SCT-Aa18 | GYTFISYV (48) | IIPYNDGT (74) | AKWGNWDEGTWFPY (92) | QSIVHSDGNTY (59) | KIS (84) | FQGSHVPWT (103) |
| SCT-Aa19 | GCTFTDYY (49) | IYPGNLNS (75) | ARYNYEGYFDY (93) | QSIADS (60) | YAS (81) | QNGHSFPLT (104) |

TABLE 12

| | VH and VL sequences of murine anti-BCMA antibodies | | | |
|---|---|---|---|---|
| mAb AA ID | VH Amino Acid Sequence | SEQ ID NO: | VL Amino Acid Sequence | SEQ ID NO: |
| SCT-Aa01 | DVQLQESGPGLVKPSQSLSLTCSVTGYSITSGYYWNWIRQFPGNKLEWMGYIRYDGSNNYNPSLKNRISITRDTSKNQFFLKLNSVTTEDTATYYCAPYDYDYAMDFWGQGTSVTVSS | 4 | DIQMTQSPASLSASVGETVTITCRASGNIHNYLAWYQQKQGKSPQLLVYNAKTLAHGVPSRFSGSGSGTQYSLKITSLQPEDFGTYYCQHFWSTPFTFGSGTKLEIK | 5 |
| SCT-Aa02 | EVKLLQSGGGLVQPGGSLKLSCAASGIDFSRYWMSWVRRAPGKGLEWIGEINPDSSTINSAPSLEDKFIISRDNAKNTLYLQMSKVRSEDTALYYCASLYYDYERDYAMDYWGQGASVTVSS | 6 | DIVMTQSQKFMSTSVGDRVSVTCKASQNVGTNVAWYQQKPGQSPKALIYSASYRFSGVPDRFTGSGSGTDFTLTISNVQSEDLAEYFCQQYHSYPFTFGGGTKLEIK | 7 |
| SCT-Aa03 | EVKLLQSGGGLVQPGGSLKLSCAASGIDFSRYWMSWVRRAPGKGLEWIGEINPDSSTINYAPSLKDKFIISRDNAKNTLYLQMSKVRSEDTALYYCASFYYDYDHAMDYWGQGTSVTVSS | 8 | DIVMTQSQKFMSTSVGDRFSVTCKASQNVGTNVAWYQQKPGQSPKALIYSASYRFSGVPDRFTGSGSGTDFTLTISNVQSEDLAEYFCQQYNSYPFTFGGGTKLEIK | 9 |
| SCT-Aa04 | EVKLLQSGGGLVQPGGSLKLSCAASGIDFSRYWMSWVRRAPGKGLEWIGEINPDSSTINYAPSLKDKFIISRDNAKNTLYLQMSKVRSEDTALYYCASFYYDYDRGAAMDYWGQGTSVTVSS | 10 | DIVMTQSQKFMSTSVGDRVSVTCKASQNVGTNVAWYQQKPGQSPKALIYSASYRYSGVPDRFTGSGSGTDFTLTISNVQSEDLAEYFCQQYNSYPYTFGGGTKLEIK | 11 |
| SCT-Aa05 | EVKLLQSGGGLVQPGGSLKLSCAASGIDFSRYWMSWVRRAPGKGLEWIGEINPDSSTINYAPSLKDKFIISRDNAKNTLYLQMSKVRSEDTGLYYCASLYYDYEREYGMDYWGQGTSVTVSS | 12 | DIVMTQSQKFMSTSVGDRVSVTCKASQNVGTNVAWYQQKPGQSPKALIYSASYRFSGVPDRFTGSGSGTDFTLTISNVQSEDLAEYFCQQYNSYPYTFGGGTKLEIK | 13 |
| SCT-Aa06 | EVQLQQSGPELVKPGNSVKISCKASGYSFTGYFMNWVMQSHGKSLEWIGRINPYNGDTFYNQKFKGKATLTVDKSSSTAHMELRSLTSEDSAVYYCARLDYTNYNSYPMDYWGQGTSVTVSS | 14 | DIQMTHTTSSLSASLGDRVTISCSASQGISNYLNWYLQKPDGTVKLLIYYTSNLHSGVPSRFSGSGSGTDFSLTISNLQPEDIATYYCQQYSKFPWTFGGGTKLEIK | 15 |
| SCT-Aa07 | QVQLQQSDAELVKPGASVKISCKVSGYSFTDHTIHWMKQRPEQGLEWIGYIYPRDGSTKYSEKFKGKATLTADKSSSTAYMQLNSLTSEDSAVYFCARWDYEGFDCWGQGTILTVSS | 16 | DIVMTQSPAILSVTPGDRVSLSCRASQRISDYLHWYQQKSHESPRLLIKYASQSISGIPSRFSGSGSGSDFTLSINSVEPEDVGVYYCQNGHSFPPTFGSGTKLEIK | 17 |
| SCT-Aa08 | QVQLQQSDAELVKPGASVKISCKVSGYTFIDHTIHWMKQRPEQGLEWIGYIYPRIDSSKCNEKFKDKATLTADKSSNTAYIQLNSLTSEDSAVYFCARWDYEGFDWGQGTTLTVSS | 18 | DIVMTQSPATLSVTPGDRVSLSCRASQSISDYLHWYQQKSHESPRLLIKYASQSISGIPSRFSGSGSGSDFTLSINSVEPEDVGVYYCQNGHSFPPTFGSGTKLEIK | 19 |
| SCT-Aa09 | QVQLQQSDAELVKPGASVKISCKVSGYTFTDHTIHWMKQRPEQGLEWIGYFYPRDDNTKYNEKFKGKATLTA | 20 | DIVMTQSPATLSVTPGDRVSLSCRASQSIRDYLHWYQQKSHESPRLLIKYASQSISGIPSRFSGSGSGSDFT | 21 |

TABLE 12-continued

VH and VL sequences of murine anti-BCMA antibodies

| mAb AA ID | VH Amino Acid Sequence | SEQ ID NO: | VL Amino Acid Sequence | SEQ ID NO: |
|---|---|---|---|---|
| | DRSSSTAYMQLNSLTSEDSAVYFC ARWDYEGFDYWGQGTTLTVSS | | LSINSVEPEDVGVYYCQNGHSFPP TFGSGTKLEIK | |
| SCT-Aa10 | QVQLQQSDAELVKPGASVKISCKV SGYTFTDHTIHWMKQRPEQGLEWI GYIFPRDGNTKYNEKFKGKATMTA DKSSSTAYMQLNSLTSEDSAVYFC ARWDYEGFDCWGQGTTLTVSS | 22 | DIVMTQSPATLSVTPGDRVSLSCR ASQSISDYLHWYQQKSHESPRLLI KYASQSISGIPSRFSGSGSGSDFT LSINSVEPEDVGVYFCQNGHSFPP TFGSGTKLEIK | 23 |
| SCT-Aa11 | QVQLQQSDAELVKPGASVKISCKV SGYTFTDHTIHWMKQRPEQGLEWI GYIFPRDGTTKFNEMFKGKATLTA DKSSSTAYMELNSLTSEDSAVYFC ARWDYEGFDYWGQGTTLTVSS | 24 | DIVMTQSPATLSVTPGDRVSLSCR ASQSISDYLHWYQQKSHESPRLLI KYASQFISGIPSRFRGSGSGSDFT LSINSVEPEDVGVYYCQNGHSFPP TFGSGTKLEIK | 25 |
| SCT-Aa12 | QVQLQQSDAELVKPGASVKISCKV SGYTFTDYTIHWMKQRPEQGLEWI GYIFPSDGSTKYNEKFKGKATLTA DKSSSTAYMQLNSLTSDDSAVYFC ARWDYEGFDYWGQGTTLTVSS | 26 | DIVMTQSPATLSVTPGDRVSLSCR ASQSISDYLNWYQQKSHESPRLLI KYASQSISGIPSRFSGSGSGSDFT LSINSVEPEDVGVYYCQNGHSFPP TFGSGTKLEIK | 27 |
| SCT-Aa13 | QVQLQQSDAELVKPGASVKISCKV SGYTFTDYTIHWMKQRPEQGLEWI GYIYPRDGSTKYNEKFKGKATLTA DKSSSTAYMQLNSLTSEDSAVYFC ARWDYEGFDYWGQGTTLTVSS | 28 | DIVMTQSPATLSVTPGDRVSLSCR ASQSISDYLHWYQQKSHESPRLLI KYASQSISGIPSRFSGSGSGSDFT LSINSVEPEDVGVYYCQNGHSFPP TFGSGTKLEIK | 19 |
| SCT-Aa14 | QVQLQQSDAELVKPGASVKISCKV SSYTFTDHTIHWMKQRPEQGLEWI GYIFPRDGSTKYNEKFKGKATLTA DKSSSTAYMQLNSLTSEDSAVYFC ARWDYEGFDYWGQGTTLTVSS | 29 | DIVMTQSPATLSVTPGDRVSLSCR ASQNISDYLHWYQQKSHESPRLLI KYASQSISGIPSRFSGSGSGSDFT LSINSVEPEDVGVYYCQNGHSFPP TFGSGTKLEIK | 30 |
| SCT-Aa15 | QVQLQQSDAELVKPGPSVKISCKV SGSTFTDHTVHWMKQRPEQGLEWI GYVYPRDGSTRYNEKFKGKATLTA DKSSSTAYMQLNSLTSEDSAVYFC ARWDYEGFDYWGQGTTLTVSS | 31 | DIVMTQSPATLSVTPGDRVSLSCR ASQNISDYLHWYQQKSHESPRLLI KYASQSISGIPSRFSGSGSGSDFT LSINSVEPEDVGVYYCQNGHSFPP TFGSGTKLKIK | 32 |
| SCT-Aa16 | EVQLQQSGPELVKPGASVKMSCKG SGYTFTNYIMHWVKQKPGQGLEWI GYIIPYNDNTKYNEKFKGKATLTS DKSSSTAYMELSSLTSEDSAVYYC ATYEYDVGLDYWGQGTTLTVSS | 33 | DLQMTQTTSSLSASLGDRVTISCS ARQGIVNYLNWYQQKPDGTVKLLI YNTSSLHSGVPSRFSGSGSGTDYS LTISNLEPEDIATYYCQQYSKLPW TFGGGTKLEIK | 34 |
| SCT-Aa17 | EVQLQQSGPELVKPGASVKMSCKA SGYTFTSYVMDWVKQKPGQGLEWI GYINPYNDGTKYNEKFKGKATLTS DKSSSTVYMELSSLTSEDSAVYHC ARSDYDYGYAMDYWGQGTSVTVSS | 35 | DIQMTQSPASLSLSVGETVTITCR ASENIYSNLAWYQQKQGNSPQLLV YSATHLADGVPSRFSGSGSGTQYS LKINSLQSEDFGCYYCQHFWGPPW TFGGGTKLEIK | 36 |
| SCT-Aa18 | EVQLQQSGPELVKPGASVKISCKA SGYTFISYVMHWVKQKPGQGLEWI GYIIPYNDGTKYNEKFKGKATLTS DKSSSTAYMELSSLTSEDSAVYYC AKWGNWDEGTWFPYWGQGTLVTVSA | 37 | DVLMTQTPLSLPVSLGDQASFSCR SSQSIVHSDGNTYLEWYLQKPGQS PKLLIYKISNRFSGVPDRFSGSGS GTDFTLKISRVEAEDLGVYYCFQG SHVPWTFGGGTKLEIK | 38 |
| SCT-Aa19 | QVQLQQSGPELVKPGASVRISCKA SGCTFTDYYIHWVKQRPGQGLEWI GWIYPGNLNSKENEKERDKATLTA DNSSSTAYMQLSSLTSEDSAVYFC ARYNYEGYFDYWGQGTTLTVSS | 39 | DIVMTQSPATLSVTPGDRVSLSCR ASQSIADSLHWYQQKSHESPRLLI KYASHSISGIPSRFRGSGSGSDFT LSINSVEPEDVGVYYCQNGHSFPL TFGAGTKLELK | 40 |

The preceding merely illustrates the principles of the disclosure. It will be appreciated that those skilled in the art will be able to devise various arrangements which, although not explicitly described or shown herein, embody the principles of the disclosure and are included within its spirit and scope. Furthermore, all examples and conditional language recited herein are principally intended to aid the reader in understanding the principles and concepts of the disclosure, further the art, and are to be construed as being without limitation to such specifically recited examples and conditions. Moreover, all statements herein reciting principles, aspects, and embodiments of the disclosure as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present disclosure, therefore, is not intended to be limited to the exemplary embodiments shown and described herein. Rather, the scope and spirit of present disclosure is embodied by the appended claims.

REFERENCES

Chiu, A., Xu, W., He, B., Dillon, S. R., Gross, J. A., Sievers, E., Qiao, X., Santini, P., Hyjek, E., Lee, J., Cesarman, E., Chadburn, A., Knowles, D. M., and Cerutti, A. (2007). Hodgkin lymphoma cells express TACI and BCMA receptors and generate survival and proliferation signals in response to BAFF and APRIL. Blood 109(2):729-39.

Hatzoglou, A., Roussel, J., Bourgeade, M. F., Rogier, E., Madry, C., Inoue, J., Devergne, O., and Tsapis, A. (2000). TNF receptor family member BCMA (B cell maturation) associates with TNF receptor-associated factor (TRAF) 1, TRAF2, and TRAF3 and activates NF-kappa B, elk-1, c-Jun N-terminal kinase, and p38 mitogen-activated protein kinase. J. Immunol. 165(3): 1322-30.

He, B., Chadburn, A., Jou, E., Schattner, E. J., Knowles, D. M., and Cerutti, A. (2004). Lymphoma B cells evade apoptosis through the TNF family members BAFF/BLyS and APRIL. J. Immunol. 172(5):3268-79.

Huang, X., Di Liberto, M., Cunningham, A. F., Kang, L., Cheng, S., Ely, S., Liou, H., Maclennan, I. C. M., and Chen-Kiang, S. (2004). Homeostatic cell-cycle control by BLyS: Induction of cell-cycle entry but not G1/S transition in opposition to p18INK4c and p27Kip1. Proc. Natl. Acad. Sci. U.S.A. 101(51):17789-94.

Kalled, S. L., Ambrose, C., and Hsu, Y.-M. (2005). The biochemistry and biology of BAFF, APRIL and their receptors. Curr. Dir. Autoimmun. 8:206-42.

Litinskiy, M. B., Nardelli, B., Hilbert, D. M., He, B., Schaffer, A., Casali, P., and Cerutti, A. (2002). DCs induce CD40-independent immunoglobulin class switching through BLyS and APRIL. Nat. Immunol. 3(9):822-9.

Novak, A. J., Darce, J. R., Arendt, B. K., Harder, B., Henderson, K., Kindsvogel, W., Gross, J. A., Greipp, P. R., and Jelinek, D. F. (2004a). Expression of BCMA, TACI, and BAFF-R in multiple myeloma: a mechanism for growth and survival. Blood 103(2):689-94.

Novak, A. J., Grote, D. M., Stenson, M., Ziesmer, S. C., Witzig, T. E., Habermann, T. M., Harder, B., Ristow, K. M., Bram, R. J., Jelinek, D. F., et al. (2004b). Expression of BLyS and its receptors in B-cell non-Hodgkin lymphoma: correlation with disease activity and patient outcome. Blood 104(8):2247-53.

O'Connor, B. P., Raman, V. S., Erickson, L. D., Cook, W. J., Weaver, L. K., Ahonen, C., Lin, L.-L., Mantchev, G. T., Bram, R. J., and Noelle, R. J. (2004). BCMA is essential for the survival of long-lived bone marrow plasma cells. J. Exp. Med. 199(1):91-8.

Pomerantz, J. L., and Baltimore, D. (2002). Two pathways to NF-kappaB. Mol. Cell 10(4):693-5.

Schiemann, B., Gommerman, J. L., Vora, K., Cachero, T. G., Shulga-Morskaya, S., Dobles, M., Frew, E., and Scott, M. L. (2001). An essential role for BAFF in the normal development of B cells through a BCMA-independent pathway. Science 293(5537):2111-4.

Xu, S., and Lam, K. P. (2001). B-cell maturation protein, which binds the tumor necrosis factor family members BAFF and APRIL, is dispensable for humoral immune responses. Mol. Cell. Biol. 21(12):4067-74.

What is claimed is:

1. An antibody that binds human BCMA comprising SEQ ID NO:1, the antibody comprising:

a) a HCDR1 comprising the amino acid sequence of SEQ ID NO:50, a HCDR2 comprising the amino acid sequence of SEQ ID NO:76, a HCDR3 comprising the amino acid sequence of SEQ ID NO:94, a LCDR1 comprising the amino acid sequence of SEQ ID NO:61, a LCDR2 comprising the amino acid sequence of SEQ ID NO:85, and a LCDR3 comprising the amino acid sequence of SEQ ID NO: 105; or b) a HCDR1 comprising the amino acid sequence of SEQ ID NO:50, a HCDR2 comprising the amino acid sequence of SEQ ID NO:76, a HCDR3 comprising the amino acid sequence of SEQ ID NO:95, a LCDR1 comprising the amino acid sequence of SEQ ID NO:61, a LCDR2 comprising the amino acid sequence of SEQ ID NO:85, and a LCDR3 comprising the amino acid sequence of SEQ ID NO:106; or c) a HCDR1 comprising the amino acid sequence of SEQ ID NO:50, a HCDR2 comprising the amino acid sequence of SEQ ID NO:76, a HCDR3 comprising the amino acid sequence of SEQ ID NO:96, a LCDR 1 comprising the amino acid sequence of SEQ ID NO:61, a LCDR2 comprising the amino acid sequence of SEQ ID NO:85, and a LCDR3 comprising the amino acid sequence of SEQ ID NO: 107; or d) a HCDR1 comprising the amino acid sequence of SEQ ID NO:50, a HCDR2 comprising the amino acid sequence of SEQ ID NO:76, a HCDR3 comprising the amino acid sequence of SEQ ID NO:97, a LCDR1 comprising the amino acid sequence of SEQ ID NO:61, a LCDR2 comprising the amino acid sequence of SEQ ID NO:85, and a LCDR3 comprising the amino acid sequence of SEQ ID NO: 107; or e) a HCDR1 comprising the amino acid sequence of SEQ ID NO:46, a HCDR2 comprising the amino acid sequence of SEQ ID NO: 72, a HCDR3 comprising the amino acid sequence of SEQ ID NO:90, a LCDR 1 comprising the amino acid sequence of SEQ ID NO:57, a LCDR2 comprising the amino acid sequence of SEQ ID NO:82, and a LCDR3 comprising the amino acid sequence of SEQ ID NO: 101; or f) a HCDR1 comprising the amino acid sequence of SEQ ID NO:48, a HCDR2 comprising the amino acid sequence of SEQ ID NO:74, a HCDR3 comprising the amino acid sequence of SEQ ID NO:92, a LCDR1 comprising the amino acid sequence of SEQ ID NO:59, a LCDR2 comprising the amino acid sequence of SEQ ID NO:84, and a LCDR3 comprising the amino acid sequence of SEQ ID NO:103.

2. The antibody of claim 1, wherein the $V_H$ comprises the amino acid sequence of SEQ ID NO:6 or a sequence that is at least 80% identical thereto, and the $V_L$ comprises the amino acid sequence of SEQ ID NO:7 or a sequence that is at least 80% identical thereto.

3. The antibody of claim 1, wherein the $V_H$ comprises the amino acid sequence of SEQ ID NO:8 or a sequence that is at least 80% identical thereto, and the $V_L$ comprises the amino acid sequence of SEQ ID NO:9 or a sequence that is at least 80% identical thereto.

4. The antibody of claim 1, wherein the $V_H$ comprises the amino acid sequence of SEQ ID NO: 10 or a sequence that is at least 80% identical thereto, and the $V_L$ comprises the amino acid sequence of SEQ ID NO: 11 or a sequence that is at least 80% identical thereto.

5. The antibody of claim 1, wherein the $V_H$ comprises the amino acid sequence of SEQ ID NO: 12 or a sequence that is at least 80% identical thereto, and the $V_L$ comprises the amino acid sequence of SEQ ID NO: 13 or a sequence that is at least 80% identical thereto.

6. The antibody of claim 1, wherein the $V_H$ comprises the amino acid sequence of SEQ ID NO:33 or a sequence that is at least 80% identical thereto, and the $V_L$ comprises the amino acid sequence of SEQ ID NO:34 or a sequence that is at least 80% identical thereto.

7. The antibody of claim 1, wherein the $V_H$ comprises the amino acid sequence of SEQ ID NO:37 or a sequence that is at least 80% identical thereto, and the $V_L$ comprises the amino acid sequence of SEQ ID NO:38 or a sequence that is at least 80% identical thereto.

8. The antibody of claim 1, wherein the heavy-chain comprises the amino acid sequence of SEQ ID NO:6 or a sequence that is at least 80% identical thereto, and the light-chain comprises the amino acid sequence of SEQ ID NO:7 or a sequence that is at least 80% identical thereto.

9. The antibody of claim 1, wherein the heavy-chain comprises the amino acid sequence of SEQ ID NO:8 or a sequence that is at least 80% identical thereto, and the light-chain comprises the amino acid sequence of SEQ ID NO:9 or a sequence that is at least 80% identical thereto.

10. The antibody of claim 1, wherein the heavy-chain comprises the amino acid sequence of SEQ ID NO: 10 or a sequence that is at least 80% identical thereto, and the light-chain comprises the amino acid sequence of SEQ ID NO:11 or a sequence that is at least 80% identical thereto.

11. The antibody of claim 1, wherein the heavy-chain comprises the amino acid sequence of SEQ ID NO: 12 or a sequence that is at least 80% identical thereto, and the light-chain comprises the amino acid sequence of SEQ ID NO:13 or a sequence that is at least 80% identical thereto.

12. The antibody of claim 1, wherein the heavy-chain comprises the amino acid sequence of SEQ ID NO:33 or a sequence that is at least 80% identical thereto, and the light-chain comprises the amino acid sequence of SEQ ID NO:34 or a sequence that is at least 80% identical thereto.

13. The antibody of claim 1, wherein the heavy-chain comprises the amino acid sequence of SEQ ID NO:37 or a sequence that is at least 80% identical thereto, and the light-chain comprises the amino acid sequence of SEQ ID NO:38 or a sequence that is at least 80% identical thereto.

14. A pharmaceutical composition comprising the antibody of claim 1.

15. A kit comprising the antibody of claim 1.

16. A method of treating a BCMA-related cancer comprising administering to a subject in need thereof a therapeutically-effective amount of the antibody of claim 1 or an antigen binding fragment thereof.

17. A method of targeting a chemotherapeutic or radiotherapeutic to a BCMA-expressing cancer cell comprising administering to a subject in need thereof a therapeutically-effective amount of the antibody of claim 1 or an antigen binding fragment thereof conjugated to the chemotherapeutic or radiotherapeutic, or a pharmaceutical composition comprising the conjugated antibody or antigen binding fragment thereof.

18. A method of detecting BCMA in vitro comprising incubating the antibody of claim 1 with a sample comprising BCMA, or an antigen thereof, and detecting BCMA bound to the antibody.

19. An antibody that binds human BCMA comprising SEQ ID NO:1, the antibody comprising:
a) a $V_H$ comprising the amino acid sequence of SEQ ID NO:6, and a $V_L$ comprising the amino acid sequence of SEQ ID NO:7; or
b) a $V_H$ comprising the amino acid sequence of SEQ ID NO:8, and a $V_L$ comprising the amino acid sequence of SEQ ID NO:9; or
c) a $V_H$ comprising the amino acid sequence of SEQ ID NO:10, and a $V_L$ comprising the amino acid sequence of SEQ ID NO:11; or
d) a $V_H$ comprising the amino acid sequence of SEQ ID NO:12, and a $V_L$ comprising the amino acid sequence of SEQ ID NO: 13; or
e) a $V_H$ comprising the amino acid sequence of SEQ ID NO:33, and a $V_L$ comprising the amino acid sequence of SEQ ID NO:34; or
f) a $V_H$ comprising the amino acid sequence of SEQ ID NO:37, and a $V_L$ comprising the amino acid sequence of SEQ ID NO:38.

20. An antibody that binds human BCMA comprising SEQ ID NO:1, the antibody comprising:
a) a heavy-chain comprising the amino acid sequence of SEQ ID NO:6 and a light-chain comprising the amino acid sequence of SEQ ID NO:7; or
b) a heavy-chain comprising the amino acid sequence of SEQ ID NO:8 and a light-chain comprising the amino acid sequence of SEQ ID NO:9; or
c) a heavy-chain comprising the amino acid sequence of SEQ ID NO:10 and a light-chain comprising the amino acid sequence of SEQ ID NO:11; or
d) a heavy-chain comprising the amino acid sequence of SEQ ID NO: 12 and a light-chain comprising the amino acid sequence of SEQ ID NO:13; or
e) a heavy-chain comprising the amino acid sequence of SEQ ID NO:33 and a light-chain comprising the amino acid sequence of SEQ ID NO:34; or
f) a heavy-chain comprising the amino acid sequence of SEQ ID NO:37 and a light-chain comprising the amino acid sequence of SEQ ID NO:38.

* * * * *

SEQUENCE LISTING

```
<160> NUMBER OF SEQ ID NOS: 110

<210> SEQ ID NO 1
<211> LENGTH: 184
<212> TYPE: PRT
<213> ORGANISM: Homo sapiens

<400> SEQUENCE: 1

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125
```

```
Glu Asp Cys Ile Lys Ser Lys Pro Lys Val Asp Ser Asp His Cys Phe
            130                 135                 140

Pro Leu Pro Ala Met Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 2
<211> LENGTH: 72
<212> TYPE: PRT
<213> ORGANISM: Artificial Sequence
<220> FEATURE:
<223> OTHER INFORMATION: Engineered

<400> SEQUENCE: 2

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Gly Gly Ser Gly Gly Ser His His
50                  55                  60

His His His His His His His His
65                  70

<210> SEQ ID NO 3
<211> LENGTH: 286
<212> TYPE: PRT
<213> ORGANISM: Artificial Sequence
<220> FEATURE:
<223> OTHER INFORMATION: Engineered

<400> SEQUENCE: 3

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
                20                  25                  30

Pro Pro Leu Thr Cys Gln Arg Tyr Cys Asn Ala Ser Val Thr Asn Ser
            35                  40                  45

Val Lys Gly Thr Asn Ala Glu Pro Lys Ser Cys Asp Lys Thr His Thr
50                  55                  60

Cys Pro Pro Cys Pro Ala Pro Glu Leu Leu Gly Gly Pro Ser Val Phe
65                  70                  75                  80

Leu Phe Pro Pro Lys Pro Lys Asp Thr Leu Met Ile Ser Arg Thr Pro
            85                  90                  95

Glu Val Thr Cys Val Val Val Asp Val Ser His Glu Asp Pro Glu Val
                100                 105                 110

Lys Phe Asn Trp Tyr Val Asp Gly Val Glu Val His Asn Ala Lys Thr
            115                 120                 125

Lys Pro Arg Glu Glu Gln Tyr Asn Ser Thr Tyr Arg Val Val Ser Val
            130                 135                 140

Leu Thr Val Leu His Gln Asp Trp Leu Asn Gly Lys Glu Tyr Lys Cys
145                 150                 155                 160

Lys Val Ser Asn Lys Ala Leu Pro Ala Pro Ile Glu Lys Thr Ile Ser
```

```
                165                 170                 175
Lys Ala Lys Gly Gln Pro Arg Glu Pro Gln Val Tyr Thr Leu Pro Pro
            180                 185                 190

Ser Arg Asp Glu Leu Thr Lys Asn Gln Val Ser Leu Thr Cys Leu Val
        195                 200                 205

Lys Gly Phe Tyr Pro Ser Asp Ile Ala Val Glu Trp Glu Ser Asn Gly
    210                 215                 220

Gln Pro Glu Asn Asn Tyr Lys Thr Thr Pro Pro Val Leu Asp Ser Asp
225                 230                 235                 240

Gly Ser Phe Phe Leu Tyr Ser Lys Leu Thr Val Asp Lys Ser Arg Trp
            245                 250                 255

Gln Gln Gly Asn Val Phe Ser Cys Ser Val Met His Glu Ala Leu His
        260                 265                 270

Asn His Tyr Thr Gln Lys Ser Leu Ser Leu Ser Pro Gly Lys
    275                 280                 285

<210> SEQ ID NO 4
<211> LENGTH: 118
<212> TYPE: PRT
<213> ORGANISM: Mus musculus

<400> SEQUENCE: 4

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Arg Tyr Asp Gly Ser Asn Asn Tyr Asn Pro Ser Leu
    50                  55                  60

Lys Asn Arg Ile Ser Ile Thr Arg Asp Thr Ser Lys Asn Gln Phe Phe
65                  70                  75                  80

Leu Lys Leu Asn Ser Val Thr Thr Glu Asp Thr Ala Thr Tyr Tyr Cys
                85                  90                  95

Ala Pro Tyr Asp Tyr Asp Tyr Ala Met Asp Phe Trp Gly Gln Gly Thr
            100                 105                 110

Ser Val Thr Val Ser Ser
        115

<210> SEQ ID NO 5
<211> LENGTH: 107
<212> TYPE: PRT
<213> ORGANISM: Mus musculus

<400> SEQUENCE: 5

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala His Gly Val Pro Ser Arg Phe Ser Gly
    50                  55                  60

Ser Gly Ser Gly Thr Gln Tyr Ser Leu Lys Ile Thr Ser Leu Gln Pro
65                  70                  75                  80

Glu Asp Phe Gly Thr Tyr Tyr Cys Gln His Phe Trp Ser Thr Pro Phe
```

```
                    85                  90                  95

Thr Phe Gly Ser Gly Thr Lys Leu Glu Ile Lys
                100                 105

<210> SEQ ID NO 6
<211> LENGTH: 122
<212> TYPE: PRT
<213> ORGANISM: Mus musculus

<400> SEQUENCE: 6

Glu Val Lys Leu Leu Gln Ser Gly Gly Gly Leu Val Gln Pro Gly Gly
1               5                   10                  15

Ser Leu Lys Leu Ser Cys Ala Ala Ser Gly Ile Asp Phe Ser Arg Tyr
            20                  25                  30

Trp Met Ser Trp Val Arg Arg Ala Pro Gly Lys Gly Leu Glu Trp Ile
        35                  40                  45

Gly Glu Ile Asn Pro Asp Ser Ser Thr Ile Asn Ser Ala Pro Ser Leu
    50                  55                  60

Glu Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Ser Leu Tyr Tyr Asp Tyr Glu Arg Asp Tyr Ala Met Asp Tyr Trp
                100                 105                 110

Gly Gln Gly Ala Ser Val Thr Val Ser Ser
            115                 120

<210> SEQ ID NO 7
<211> LENGTH: 107
<212> TYPE: PRT
<213> ORGANISM: Mus musculus

<400> SEQUENCE: 7

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Phe Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr His Ser Tyr Pro Phe
                85                  90                  95

Thr Phe Gly Gly Gly Thr Lys Leu Glu Ile Lys
                100                 105

<210> SEQ ID NO 8
<211> LENGTH: 120
<212> TYPE: PRT
<213> ORGANISM: Mus musculus

<400> SEQUENCE: 8

Glu Val Lys Leu Leu Gln Ser Gly Gly Gly Leu Val Gln Pro Gly Gly
1               5                   10                  15

Ser Leu Lys Leu Ser Cys Ala Ala Ser Gly Ile Asp Phe Ser Arg Tyr
            20                  25                  30
```

```
Trp Met Ser Trp Val Arg Arg Ala Pro Gly Lys Gly Leu Glu Trp Ile
            35                  40                  45

Gly Glu Ile Asn Pro Asp Ser Ser Thr Ile Asn Tyr Ala Pro Ser Leu
 50                  55                  60

Lys Asp Lys Phe Ile Ile Ser Arg Asp Asn Ala Lys Asn Thr Leu Tyr
 65                  70                  75                  80

Leu Gln Met Ser Lys Val Arg Ser Glu Asp Thr Ala Leu Tyr Tyr Cys
                 85                  90                  95

Ala Ser Phe Tyr Tyr Asp Tyr Asp His Ala Met Asp Tyr Trp Gly Gln
                100                 105                 110

Gly Thr Ser Val Thr Val Ser Ser
                115                 120

<210> SEQ ID NO 9
<211> LENGTH: 107
<212> TYPE: PRT
<213> ORGANISM: Mus musculus

<400> SEQUENCE: 9

Asp Ile Val Met Thr Gln Ser Gln Lys Phe Met Ser Thr Ser Val Gly
 1               5                  10                  15

Asp Arg Phe Ser Val Thr Cys Lys Ala Ser Gln Asn Val Gly Thr Asn
                 20                  25                  30

Val Ala Trp Tyr Gln Gln Lys Pro Gly Gln Ser Pro Lys Ala Leu Ile
             35                  40                  45

Tyr Ser Ala Ser Tyr Arg Phe Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Phe
                 85                  90                  95

Thr Phe Gly Ser Gly Thr Lys Leu Glu Ile Lys
                100                 105

<210> SEQ ID NO 10
<211> LENGTH: 122
<212> TYPE: PRT
<213> ORGANISM: Mus musculus

<400> SEQUENCE: 10

Glu Val Lys Leu Leu Gln Ser Gly Gly Gly Leu Val Gln Pro Gly Gly
 1               5                  10                  15

Ser Leu Lys Leu Ser Cys Ala Ala Ser Gly Ile Asp Phe Ser Arg Tyr
                 20                  25                  30

Trp Met Ser Trp Val Arg Arg Ala Pro Gly Lys Gly Leu Glu Trp Ile
            35                  40                  45

Gly Glu Ile Asn Pro Asp Ser Ser Thr Ile Asn Tyr Ala Pro Ser Leu
 50                  55                  60

Lys Asp Lys Phe Ile Ile Ser Arg Asp Asn Ala Lys Asn Thr Leu Tyr
 65                  70                  75                  80

Leu Gln Met Ser Lys Val Arg Ser Glu Asp Thr Ala Leu Tyr Tyr Cys
                 85                  90                  95

Ala Ser Phe Tyr Tyr Asp Tyr Asp Arg Gly Ala Ala Met Asp Tyr Trp
                100                 105                 110

Gly Gln Gly Thr Ser Val Thr Val Ser Ser
                115                 120
```

<210> SEQ ID NO 11
<211> LENGTH: 107
<212> TYPE: PRT
<213> ORGANISM: Mus musculus

<400> SEQUENCE: 11

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
            100                 105

<210> SEQ ID NO 12
<211> LENGTH: 122
<212> TYPE: PRT
<213> ORGANISM: Mus musculus

<400> SEQUENCE: 12

Glu Val Lys Leu Leu Gln Ser Gly Gly Gly Leu Val Gln Pro Gly Gly
1               5                   10                  15

Ser Leu Lys Leu Ser Cys Ala Ala Ser Gly Ile Asp Phe Ser Arg Tyr
            20                  25                  30

Trp Met Ser Trp Val Arg Arg Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Gly Leu Tyr Tyr Cys
                85                  90                  95

Ala Ser Leu Tyr Tyr Asp Tyr Glu Arg Glu Tyr Gly Met Asp Tyr Trp
            100                 105                 110

Gly Gln Gly Thr Ser Val Thr Val Ser Ser
        115                 120

<210> SEQ ID NO 13
<211> LENGTH: 107
<212> TYPE: PRT
<213> ORGANISM: Mus musculus

<400> SEQUENCE: 13

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

```
Tyr Ser Ala Ser Tyr Arg Phe Ser Gly Val Pro Asp Arg Phe Thr Gly
        50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Tyr
                85                  90                  95

Thr Phe Gly Gly Gly Thr Lys Leu Glu Ile Lys
                100                 105

<210> SEQ ID NO 14
<211> LENGTH: 122
<212> TYPE: PRT
<213> ORGANISM: Mus musculus

<400> SEQUENCE: 14

Glu Val Gln Leu Gln Gln Ser Gly Pro Glu Leu Val Lys Pro Gly Asn
1               5                   10                  15

Ser Val Lys Ile Ser Cys Lys Ala Ser Gly Tyr Ser Phe Thr Gly Tyr
                20                  25                  30

Phe Met Asn Trp Val Met Gln Ser His Gly Lys Ser Leu Glu Trp Ile
            35                  40                  45

Gly Arg Ile Asn Pro Tyr Asn Gly Asp Thr Phe Tyr Asn Gln Lys Phe
        50                  55                  60

Lys Gly Lys Ala Thr Leu Thr Val Asp Lys Ser Ser Ser Thr Ala His
65                  70                  75                  80

Met Glu Leu Arg Ser Leu Thr Ser Glu Asp Ser Ala Val Tyr Tyr Cys
                85                  90                  95

Ala Arg Leu Asp Tyr Thr Asn Tyr Asn Ser Tyr Pro Met Asp Tyr Trp
                100                 105                 110

Gly Gln Gly Thr Ser Val Thr Val Ser Ser
            115                 120

<210> SEQ ID NO 15
<211> LENGTH: 107
<212> TYPE: PRT
<213> ORGANISM: Mus musculus

<400> SEQUENCE: 15

Asp Ile Gln Met Thr His Thr Thr Ser Ser Leu Ser Ala Ser Leu Gly
1               5                   10                  15

Asp Arg Val Thr Ile Ser Cys Ser Ala Ser Gln Gly Ile Ser Asn Tyr
                20                  25                  30

Leu Asn Trp Tyr Leu Gln Lys Pro Asp Gly Thr Val Lys Leu Leu Ile
            35                  40                  45

Tyr Tyr Thr Ser Asn Leu His Ser Gly Val Pro Ser Arg Phe Ser Gly
        50                  55                  60

Ser Gly Ser Gly Thr Asp Phe Ser Leu Thr Ile Ser Asn Leu Gln Pro
65                  70                  75                  80

Glu Asp Ile Ala Thr Tyr Tyr Cys Gln Gln Tyr Ser Lys Phe Pro Trp
                85                  90                  95

Thr Phe Gly Gly Gly Thr Lys Leu Glu Ile Lys
                100                 105

<210> SEQ ID NO 16
<211> LENGTH: 117
<212> TYPE: PRT
<213> ORGANISM: Mus musculus
```

<400> SEQUENCE: 16

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Ser Phe Thr Asp His
            20                  25                  30

Thr Ile His Trp Met Lys Gln Arg Pro Glu Gln Gly Leu Glu Trp Ile
        35                  40                  45

Gly Tyr Ile Tyr Pro Arg Asp Gly Ser Thr Lys Tyr Ser Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Trp Asp Tyr Glu Gly Phe Asp Cys Trp Gly Gln Gly Thr Ile
            100                 105                 110

Leu Thr Val Ser Ser
            115

<210> SEQ ID NO 17
<211> LENGTH: 107
<212> TYPE: PRT
<213> ORGANISM: Mus musculus

<400> SEQUENCE: 17

Asp Ile Val Met Thr Gln Ser Pro Ala Ile Leu Ser Val Thr Pro Gly
1               5                   10                  15

Asp Arg Val Ser Leu Ser Cys Arg Ala Ser Gln Arg Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Pro
                85                  90                  95

Thr Phe Gly Ser Gly Thr Lys Leu Glu Ile Lys
            100                 105

<210> SEQ ID NO 18
<211> LENGTH: 117
<212> TYPE: PRT
<213> ORGANISM: Mus musculus

<400> SEQUENCE: 18

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Ile Asp His
            20                  25                  30

Thr Ile His Trp Met Lys Gln Arg Pro Glu Gln Gly Leu Glu Trp Ile
        35                  40                  45

Gly Tyr Ile Tyr Pro Arg Ile Asp Ser Ser Lys Cys Asn Glu Lys Phe
    50                  55                  60

Lys Asp Lys Ala Thr Leu Thr Ala Asp Lys Ser Ser Asn Thr Ala Tyr
65                  70                  75                  80

Ile Gln Leu Asn Ser Leu Thr Ser Glu Asp Ser Ala Val Tyr Phe Cys

```
                         85                  90                  95

Ala Arg Trp Asp Tyr Glu Gly Phe Asp Tyr Trp Gly Gln Gly Thr Thr
                100                 105                 110

Leu Thr Val Ser Ser
        115

<210> SEQ ID NO 19
<211> LENGTH: 107
<212> TYPE: PRT
<213> ORGANISM: Mus musculus

<400> SEQUENCE: 19

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Pro
                85                  90                  95

Thr Phe Gly Ser Gly Thr Lys Leu Glu Ile Lys
                100                 105

<210> SEQ ID NO 20
<211> LENGTH: 117
<212> TYPE: PRT
<213> ORGANISM: Mus musculus

<400> SEQUENCE: 20

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
        35                  40                  45

Gly Tyr Phe Tyr Pro Arg Asp Asp Asn Thr Lys Tyr Asn Glu Lys Phe
    50                  55                  60

Lys Gly Lys Ala Thr Leu Thr Ala Asp Arg Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Trp Asp Tyr Glu Gly Phe Asp Tyr Trp Gly Gln Gly Thr Thr
                100                 105                 110

Leu Thr Val Ser Ser
        115

<210> SEQ ID NO 21
<211> LENGTH: 107
<212> TYPE: PRT
<213> ORGANISM: Mus musculus

<400> SEQUENCE: 21

Asp Ile Val Met Thr Gln Ser Pro Ala Thr Leu Ser Val Thr Pro Gly
1               5                   10                  15
```

Asp Arg Val Ser Leu Ser Cys Arg Ala Ser Gln Ser Ile Arg Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Pro
                85                  90                  95

Thr Phe Gly Ser Gly Thr Lys Leu Glu Ile Lys
            100                 105

<210> SEQ ID NO 22
<211> LENGTH: 117
<212> TYPE: PRT
<213> ORGANISM: Mus musculus

<400> SEQUENCE: 22

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
        35                  40                  45

Gly Tyr Ile Phe Pro Arg Asp Gly Asn Thr Lys Tyr Asn Glu Lys Phe
50                  55                  60

Lys Gly Lys Ala Thr Met Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Trp Asp Tyr Glu Gly Phe Asp Cys Trp Gly Gln Gly Thr Thr
            100                 105                 110

Leu Thr Val Ser Ser
        115

<210> SEQ ID NO 23
<211> LENGTH: 107
<212> TYPE: PRT
<213> ORGANISM: Mus musculus

<400> SEQUENCE: 23

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Phe Cys Gln Asn Gly His Ser Phe Pro Pro
                85                  90                  95

Thr Phe Gly Ser Gly Thr Lys Leu Glu Ile Lys
            100                 105

<210> SEQ ID NO 24
<211> LENGTH: 117
<212> TYPE: PRT
<213> ORGANISM: Mus musculus

<400> SEQUENCE: 24

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp His
            20                  25                  30

Thr Ile His Trp Met Lys Gln Arg Pro Glu Gln Gly Leu Glu Trp Ile
        35                  40                  45

Gly Tyr Ile Phe Pro Arg Asp Gly Thr Thr Lys Phe Asn Glu Met Phe
    50                  55                  60

Lys Gly Lys Ala Thr Leu Thr Ala Asp Lys Ser Ser Thr Ala Tyr
65                  70                  75                  80

Met Glu Leu Asn Ser Leu Thr Ser Glu Asp Ser Ala Val Tyr Phe Cys
                85                  90                  95

Ala Arg Trp Asp Tyr Glu Gly Phe Asp Tyr Trp Gly Gln Gly Thr Thr
            100                 105                 110

Leu Thr Val Ser Ser
        115

<210> SEQ ID NO 25
<211> LENGTH: 107
<212> TYPE: PRT
<213> ORGANISM: Mus musculus

<400> SEQUENCE: 25

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Phe Ile Ser Gly Ile Pro Ser Arg Phe Arg Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Pro
                85                  90                  95

Thr Phe Gly Ser Gly Thr Lys Leu Glu Ile Lys
            100                 105

<210> SEQ ID NO 26
<211> LENGTH: 117
<212> TYPE: PRT
<213> ORGANISM: Mus musculus

<400> SEQUENCE: 26

Gln Val Gln Leu Gln Gln Ser Asp Ala Glu Leu Val Lys Pro Gly Ala
1               5                   10                  15

Ser Val Lys Ile Ser Cys Lys Val Ser Gly Tyr Thr Phe Thr Asp Tyr
            20                  25                  30

Thr Ile His Trp Met Lys Gln Arg Pro Glu Gln Gly Leu Glu Trp Ile
        35                  40                  45

```
Gly Tyr Ile Phe Pro Ser Asp Gly Ser Thr Lys Tyr Asn Glu Lys Phe
        50                  55                  60

Lys Gly Lys Ala Thr Leu Thr Ala Asp Lys Ser Ser Ser Thr Ala Tyr
 65                  70                  75                  80

Met Gln Leu Asn Ser Leu Thr Ser Asp Ser Ala Val Tyr Phe Cys
                85                  90                  95

Ala Arg Trp Asp Tyr Glu Gly Phe Asp Tyr Trp Gly Gln Gly Thr Thr
            100                 105                 110

Leu Thr Val Ser Ser
        115

<210> SEQ ID NO 27
<211> LENGTH: 107
<212> TYPE: PRT
<213> ORGANISM: Mus musculus

<400> SEQUENCE: 27

Asp Ile Val Met Thr Gln Ser Pro Ala Thr Leu Ser Val Thr Pro Gly
 1               5                  10                  15

Asp Arg Val Ser Leu Ser Cys Arg Ala Ser Gln Ser Ile Ser Asp Tyr
            20                  25                  30

Leu Asn Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Pro Pro
                85                  90                  95

Thr Phe Gly Ser Gly Thr Lys Leu Glu Ile Lys
            100                 105

<210> SEQ ID NO 28
<211> LENGTH: 117
<212> TYPE: PRT
<213> ORGANISM: Mus musculus

<400> SEQUENCE: 28

Gln Val Gln Leu Gln Gln Ser Asp Ala Glu Leu Val Lys Pro Gly Ala
 1               5                  10                  15

Ser Val Lys Ile Ser Cys Lys Val Ser Gly Tyr Thr Phe Thr Asp Tyr
            20                  25                  30

Thr Ile His Trp Met Lys Gln Arg Pro Glu Gln Gly Leu Glu Trp Ile
        35                  40                  45

Gly Tyr Ile Tyr Pro Arg Asp Gly Ser Thr Lys Tyr Asn Glu Lys Phe
    50                  55                  60

Lys Gly Lys Ala Thr Leu Thr Ala Asp Lys Ser Ser Ser Thr Ala Tyr
 65                  70                  75                  80

Met Gln Leu Asn Ser Leu Thr Ser Glu Asp Ser Ala Val Tyr Phe Cys
                85                  90                  95

Ala Arg Trp Asp Tyr Glu Gly Phe Asp Tyr Trp Gly Gln Gly Thr Thr
            100                 105                 110

Leu Thr Val Ser Ser
        115

<210> SEQ ID NO 29
<211> LENGTH: 117
```

```
<212> TYPE: PRT
<213> ORGANISM: Mus musculus

<400> SEQUENCE: 29

Gln Val Gln Leu Gln Gln Ser Asp Ala Glu Leu Val Lys Pro Gly Ala
1               5                   10                  15

Ser Val Lys Ile Ser Cys Lys Val Ser Ser Tyr Thr Phe Thr Asp His
            20                  25                  30

Thr Ile His Trp Met Lys Gln Arg Pro Glu Gln Gly Leu Glu Trp Ile
        35                  40                  45

Gly Tyr Ile Phe Pro Arg Asp Gly Ser Thr Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Trp Asp Tyr Glu Gly Phe Asp Tyr Trp Gly Gln Gly Thr Thr
            100                 105                 110

Leu Thr Val Ser Ser
            115

<210> SEQ ID NO 30
<211> LENGTH: 107
<212> TYPE: PRT
<213> ORGANISM: Mus musculus

<400> SEQUENCE: 30

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Asn Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Pro
                85                  90                  95

Thr Phe Gly Ser Gly Thr Lys Leu Glu Ile Lys
            100                 105

<210> SEQ ID NO 31
<211> LENGTH: 117
<212> TYPE: PRT
<213> ORGANISM: Mus musculus

<400> SEQUENCE: 31

Gln Val Gln Leu Gln Gln Ser Asp Ala Glu Leu Val Lys Pro Gly Pro
1               5                   10                  15

Ser Val Lys Ile Ser Cys Lys Val Ser Gly Ser Thr Phe Thr Asp His
            20                  25                  30

Thr Val His Trp Met Lys Gln Arg Pro Glu Gln Gly Leu Glu Trp Ile
        35                  40                  45

Gly Tyr Val Tyr Pro Arg Asp Gly Ser Thr Arg Tyr Asn Glu Lys Phe
    50                  55                  60

Lys Gly Lys Ala Thr Leu Thr Ala Asp Lys Ser Ser Ser Thr Ala Tyr
```

```
                65                  70                  75                  80
Met Gln Leu Asn Ser Leu Thr Ser Glu Asp Ser Ala Val Tyr Phe Cys
                    85                  90                  95

Ala Arg Trp Asp Tyr Glu Gly Phe Asp Tyr Trp Gly Gln Gly Thr Thr
                100                 105                 110

Leu Thr Val Ser Ser
        115
```

<210> SEQ ID NO 32
<211> LENGTH: 107
<212> TYPE: PRT
<213> ORGANISM: Mus musculus

<400> SEQUENCE: 32

```
Asp Ile Val Met Thr Gln Ser Pro Ala Thr Leu Ser Val Thr Pro Gly
1               5                   10                  15

Asp Arg Val Ser Leu Ser Cys Arg Ala Ser Gln Asn Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Pro
                85                  90                  95

Thr Phe Gly Ser Gly Thr Lys Leu Lys Ile Lys
            100                 105
```

<210> SEQ ID NO 33
<211> LENGTH: 118
<212> TYPE: PRT
<213> ORGANISM: Mus musculus

<400> SEQUENCE: 33

```
Glu Val Gln Leu Gln Gln Ser Gly Pro Glu Leu Val Lys Pro Gly Ala
1               5                   10                  15

Ser Val Lys Met Ser Cys Lys Gly Ser Gly Tyr Thr Phe Thr Asn Tyr
            20                  25                  30

Ile Met His Trp Val Lys Gln Lys Pro Gly Gln Gly Leu Glu Trp Ile
        35                  40                  45

Gly Tyr Ile Ile Pro Tyr Asn Asp Asn Thr Lys Tyr Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Thr Tyr Glu Tyr Asp Val Gly Leu Asp Tyr Trp Gly Gln Gly Thr
                100                 105                 110

Thr Leu Thr Val Ser Ser
        115
```

<210> SEQ ID NO 34
<211> LENGTH: 107
<212> TYPE: PRT
<213> ORGANISM: Mus musculus

<400> SEQUENCE: 34

```
Asp Leu Gln Met Thr Gln Thr Ser Ser Leu Ser Ala Ser Leu Gly
1               5                   10                  15

Asp Arg Val Thr Ile Ser Cys Ser Ala Arg Gln Gly Ile Val Asn Tyr
            20                  25                  30

Leu Asn Trp Tyr Gln Gln Lys Pro Asp Gly Thr Val Lys Leu Leu Ile
            35                  40                  45

Tyr Asn Thr Ser Ser Leu His Ser Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Trp
                85                  90                  95

Thr Phe Gly Gly Gly Thr Lys Leu Glu Ile Lys
            100                 105
```

<210> SEQ ID NO 35
<211> LENGTH: 120
<212> TYPE: PRT
<213> ORGANISM: Mus musculus

<400> SEQUENCE: 35

```
Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Val Met Asp Trp Val Lys Gln Lys Pro Gly Gln Gly Leu Glu Trp Ile
            35                  40                  45

Gly Tyr Ile Asn Pro Tyr Asn Asp Gly Thr Lys Tyr Asn Glu Lys Phe
50                  55                  60

Lys Gly Lys Ala Thr Leu Thr Ser Asp Lys Ser Ser Ser Thr Val Tyr
65                  70                  75                  80

Met Glu Leu Ser Ser Leu Thr Ser Glu Asp Ser Ala Val Tyr His Cys
                85                  90                  95

Ala Arg Ser Asp Tyr Asp Tyr Gly Tyr Ala Met Asp Tyr Trp Gly Gln
                100                 105                 110

Gly Thr Ser Val Thr Val Ser Ser
            115                 120
```

<210> SEQ ID NO 36
<211> LENGTH: 107
<212> TYPE: PRT
<213> ORGANISM: Mus musculus

<400> SEQUENCE: 36

```
Asp Ile Gln Met Thr Gln Ser Pro Ala Ser Leu Ser Leu Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Asn Ser Pro Gln Leu Leu Val
            35                  40                  45

Tyr Ser Ala Thr His Leu Ala Asp Gly Val Pro Ser Arg Phe Ser Gly
50                  55                  60

Ser Gly Ser Gly Thr Gln Tyr Ser Leu Lys Ile Asn Ser Leu Gln Ser
65                  70                  75                  80

Glu Asp Phe Gly Cys Tyr Tyr Cys Gln His Phe Trp Gly Pro Pro Trp
                85                  90                  95
```

Thr Phe Gly Gly Gly Thr Lys Leu Glu Ile Lys
            100                 105

<210> SEQ ID NO 37
<211> LENGTH: 121
<212> TYPE: PRT
<213> ORGANISM: Mus musculus

<400> SEQUENCE: 37

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Ile Ser Tyr
            20                  25                  30

Val Met His Trp Val Lys Gln Lys Pro Gly Gln Gly Leu Glu Trp Ile
        35                  40                  45

Gly Tyr Ile Ile Pro Tyr Asn Asp Gly Thr Lys Tyr Asn Glu Lys Phe
    50                  55                  60

Lys Gly Lys Ala Thr Leu Thr Ser Asp Lys Ser Ser Thr Ala Tyr
65                  70                  75                  80

Met Glu Leu Ser Ser Leu Thr Ser Glu Asp Ser Ala Val Tyr Tyr Cys
                85                  90                  95

Ala Lys Trp Gly Asn Trp Asp Glu Gly Thr Trp Phe Pro Tyr Trp Gly
            100                 105                 110

Gln Gly Thr Leu Val Thr Val Ser Ala
        115                 120

<210> SEQ ID NO 38
<211> LENGTH: 112
<212> TYPE: PRT
<213> ORGANISM: Mus musculus

<400> SEQUENCE: 38

Asp Val Leu Met Thr Gln Thr Pro Leu Ser Leu Pro Val Ser Leu Gly
1               5                   10                  15

Asp Gln Ala Ser Phe Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 39
<211> LENGTH: 118
<212> TYPE: PRT
<213> ORGANISM: Mus musculus

<400> SEQUENCE: 39

Gln Val Gln Leu Gln Gln Ser Gly Pro Glu Leu Val Lys Pro Gly Ala
1               5                   10                  15

Ser Val Arg Ile Ser Cys Lys Ala Ser Gly Cys Thr Phe Thr Asp Tyr
            20                  25                  30

```
Tyr Ile His Trp Val Lys Gln Arg Pro Gly Gln Gly Leu Glu Trp Ile
            35                  40                  45

Gly Trp Ile Tyr Pro Gly Asn Leu Asn Ser Lys Phe Asn Glu Lys Phe
 50                      55                  60

Arg Asp Lys Ala Thr Leu Thr Ala Asp Asn Ser Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Tyr Asn Tyr Glu Gly Tyr Phe Asp Tyr Trp Gly Gln Gly Thr
                100                 105                 110

Thr Leu Thr Val Ser Ser
            115
```

<210> SEQ ID NO 40
<211> LENGTH: 107
<212> TYPE: PRT
<213> ORGANISM: Mus musculus

<400> SEQUENCE: 40

```
Asp Ile Val Met Thr Gln Ser Pro Ala Thr Leu Ser Val Thr Pro Gly
 1               5                  10                  15

Asp Arg Val Ser Leu Ser Cys Arg Ala Ser Gln Ser Ile Ala Asp Ser
                 20                  25                  30

Leu His Trp Tyr Gln Gln Lys Ser His Glu Ser Pro Arg Leu Leu Ile
             35                  40                  45

Lys Tyr Ala Ser His Ser Ile Ser Gly Ile Pro Ser Arg Phe Arg Gly
 50                  55                  60

Ser Gly Ser Gly Ser Asp Phe Thr Leu Ser Ile Asn Ser Val Glu Pro
 65                  70                  75                  80

Glu Asp Val Gly Val Tyr Tyr Cys Gln Asn Gly His Ser Phe Pro Leu
                 85                  90                  95

Thr Phe Gly Ala Gly Thr Lys Leu Glu Leu Lys
                100                 105
```

<210> SEQ ID NO 41
<211> LENGTH: 9
<212> TYPE: PRT
<213> ORGANISM: Mus musculus

<400> SEQUENCE: 41

```
Gly Tyr Ser Ile Thr Ser Gly Tyr Tyr
 1               5
```

<210> SEQ ID NO 42
<211> LENGTH: 8
<212> TYPE: PRT
<213> ORGANISM: Mus musculus

<400> SEQUENCE: 42

```
Gly Tyr Thr Phe Thr Asp His Thr
 1               5
```

<210> SEQ ID NO 43
<211> LENGTH: 8
<212> TYPE: PRT
<213> ORGANISM: Mus musculus

<400> SEQUENCE: 43

```
Gly Tyr Thr Phe Thr Asp Tyr Thr
 1               5
```

```
<210> SEQ ID NO 44
<211> LENGTH: 8
<212> TYPE: PRT
<213> ORGANISM: Mus musculus

<400> SEQUENCE: 44

Ser Tyr Thr Phe Thr Asp His Thr
1               5

<210> SEQ ID NO 45
<211> LENGTH: 8
<212> TYPE: PRT
<213> ORGANISM: Mus musculus

<400> SEQUENCE: 45

Gly Ser Thr Phe Thr Asp His Thr
1               5

<210> SEQ ID NO 46
<211> LENGTH: 8
<212> TYPE: PRT
<213> ORGANISM: Mus musculus

<400> SEQUENCE: 46

Gly Tyr Thr Phe Thr Asn Tyr Ile
1               5

<210> SEQ ID NO 47
<211> LENGTH: 8
<212> TYPE: PRT
<213> ORGANISM: Mus musculus

<400> SEQUENCE: 47

Gly Tyr Thr Phe Thr Ser Tyr Val
1               5

<210> SEQ ID NO 48
<211> LENGTH: 8
<212> TYPE: PRT
<213> ORGANISM: Mus musculus

<400> SEQUENCE: 48

Gly Tyr Thr Phe Ile Ser Tyr Val
1               5

<210> SEQ ID NO 49
<211> LENGTH: 8
<212> TYPE: PRT
<213> ORGANISM: Mus musculus

<400> SEQUENCE: 49

Gly Cys Thr Phe Thr Asp Tyr Tyr
1               5

<210> SEQ ID NO 50
<211> LENGTH: 8
<212> TYPE: PRT
<213> ORGANISM: Mus musculus

<400> SEQUENCE: 50

Gly Ile Asp Phe Ser Arg Tyr Trp
1               5
```

```
<210> SEQ ID NO 51
<211> LENGTH: 8
<212> TYPE: PRT
<213> ORGANISM: Mus musculus

<400> SEQUENCE: 51

Gly Tyr Ser Phe Thr Gly Tyr Phe
1               5

<210> SEQ ID NO 52
<211> LENGTH: 8
<212> TYPE: PRT
<213> ORGANISM: Mus musculus

<400> SEQUENCE: 52

Gly Tyr Ser Phe Thr Asp His Thr
1               5

<210> SEQ ID NO 53
<211> LENGTH: 8
<212> TYPE: PRT
<213> ORGANISM: Mus musculus

<400> SEQUENCE: 53

Gly Tyr Thr Phe Ile Asp His Thr
1               5

<210> SEQ ID NO 54
<211> LENGTH: 6
<212> TYPE: PRT
<213> ORGANISM: Mus musculus

<400> SEQUENCE: 54

Gly Asn Ile His Asn Tyr
1               5

<210> SEQ ID NO 55
<211> LENGTH: 6
<212> TYPE: PRT
<213> ORGANISM: Mus musculus

<400> SEQUENCE: 55

Gln Ser Ile Ser Asp Tyr
1               5

<210> SEQ ID NO 56
<211> LENGTH: 6
<212> TYPE: PRT
<213> ORGANISM: Mus musculus

<400> SEQUENCE: 56

Gln Asn Ile Ser Asp Tyr
1               5

<210> SEQ ID NO 57
<211> LENGTH: 6
<212> TYPE: PRT
<213> ORGANISM: Mus musculus

<400> SEQUENCE: 57

Gln Gly Ile Val Asn Tyr
1               5

<210> SEQ ID NO 58
<211> LENGTH: 6
```

```
<212> TYPE: PRT
<213> ORGANISM: Mus musculus

<400> SEQUENCE: 58

Glu Asn Ile Tyr Ser Asn
1               5

<210> SEQ ID NO 59
<211> LENGTH: 11
<212> TYPE: PRT
<213> ORGANISM: Mus musculus

<400> SEQUENCE: 59

Gln Ser Ile Val His Ser Asp Gly Asn Thr Tyr
1               5                   10

<210> SEQ ID NO 60
<211> LENGTH: 6
<212> TYPE: PRT
<213> ORGANISM: Mus musculus

<400> SEQUENCE: 60

Gln Ser Ile Ala Asp Ser
1               5

<210> SEQ ID NO 61
<211> LENGTH: 6
<212> TYPE: PRT
<213> ORGANISM: Mus musculus

<400> SEQUENCE: 61

Gln Asn Val Gly Thr Asn
1               5

<210> SEQ ID NO 62
<211> LENGTH: 6
<212> TYPE: PRT
<213> ORGANISM: Mus musculus

<400> SEQUENCE: 62

Gln Gly Ile Ser Asn Tyr
1               5

<210> SEQ ID NO 63
<211> LENGTH: 6
<212> TYPE: PRT
<213> ORGANISM: Mus musculus

<400> SEQUENCE: 63

Gln Arg Ile Ser Asp Tyr
1               5

<210> SEQ ID NO 64
<211> LENGTH: 6
<212> TYPE: PRT
<213> ORGANISM: Mus musculus

<400> SEQUENCE: 64

Gln Ser Ile Arg Asp Tyr
1               5

<210> SEQ ID NO 65
<211> LENGTH: 7
<212> TYPE: PRT
<213> ORGANISM: Mus musculus
```

<400> SEQUENCE: 65

Ile Arg Tyr Asp Gly Ser Asn
1               5

<210> SEQ ID NO 66
<211> LENGTH: 8
<212> TYPE: PRT
<213> ORGANISM: Mus musculus

<400> SEQUENCE: 66

Ile Phe Pro Arg Asp Gly Asn Thr
1               5

<210> SEQ ID NO 67
<211> LENGTH: 8
<212> TYPE: PRT
<213> ORGANISM: Mus musculus

<400> SEQUENCE: 67

Ile Phe Pro Arg Asp Gly Thr Thr
1               5

<210> SEQ ID NO 68
<211> LENGTH: 8
<212> TYPE: PRT
<213> ORGANISM: Mus musculus

<400> SEQUENCE: 68

Ile Phe Pro Ser Asp Gly Ser Thr
1               5

<210> SEQ ID NO 69
<211> LENGTH: 8
<212> TYPE: PRT
<213> ORGANISM: Mus musculus

<400> SEQUENCE: 69

Ile Tyr Pro Arg Asp Gly Ser Thr
1               5

<210> SEQ ID NO 70
<211> LENGTH: 8
<212> TYPE: PRT
<213> ORGANISM: Mus musculus

<400> SEQUENCE: 70

Ile Phe Pro Arg Asp Gly Ser Thr
1               5

<210> SEQ ID NO 71
<211> LENGTH: 8
<212> TYPE: PRT
<213> ORGANISM: Mus musculus

<400> SEQUENCE: 71

Val Tyr Pro Arg Asp Gly Ser Thr
1               5

<210> SEQ ID NO 72
<211> LENGTH: 8
<212> TYPE: PRT
<213> ORGANISM: Mus musculus

<400> SEQUENCE: 72

Ile Ile Pro Tyr Asn Asp Asn Thr
1               5

<210> SEQ ID NO 73
<211> LENGTH: 8
<212> TYPE: PRT
<213> ORGANISM: Mus musculus

<400> SEQUENCE: 73

Ile Asn Pro Tyr Asn Asp Gly Thr
1               5

<210> SEQ ID NO 74
<211> LENGTH: 8
<212> TYPE: PRT
<213> ORGANISM: Mus musculus

<400> SEQUENCE: 74

Ile Ile Pro Tyr Asn Asp Gly Thr
1               5

<210> SEQ ID NO 75
<211> LENGTH: 8
<212> TYPE: PRT
<213> ORGANISM: Mus musculus

<400> SEQUENCE: 75

Ile Tyr Pro Gly Asn Leu Asn Ser
1               5

<210> SEQ ID NO 76
<211> LENGTH: 8
<212> TYPE: PRT
<213> ORGANISM: Mus musculus

<400> SEQUENCE: 76

Ile Asn Pro Asp Ser Ser Thr Ile
1               5

<210> SEQ ID NO 77
<211> LENGTH: 8
<212> TYPE: PRT
<213> ORGANISM: Mus musculus

<400> SEQUENCE: 77

Ile Asn Pro Tyr Asn Gly Asp Thr
1               5

<210> SEQ ID NO 78
<211> LENGTH: 8
<212> TYPE: PRT
<213> ORGANISM: Mus musculus

<400> SEQUENCE: 78

Ile Tyr Pro Arg Ile Asp Ser Ser
1               5

<210> SEQ ID NO 79
<211> LENGTH: 8
<212> TYPE: PRT
<213> ORGANISM: Mus musculus

<400> SEQUENCE: 79

Phe Tyr Pro Arg Asp Asp Asn Thr

```
1               5
```

<210> SEQ ID NO 80
<211> LENGTH: 3
<212> TYPE: PRT
<213> ORGANISM: Mus musculus

<400> SEQUENCE: 80

Asn Ala Lys
1

<210> SEQ ID NO 81
<211> LENGTH: 3
<212> TYPE: PRT
<213> ORGANISM: Mus musculus

<400> SEQUENCE: 81

Tyr Ala Ser
1

<210> SEQ ID NO 82
<211> LENGTH: 3
<212> TYPE: PRT
<213> ORGANISM: Mus musculus

<400> SEQUENCE: 82

Asn Thr Ser
1

<210> SEQ ID NO 83
<211> LENGTH: 3
<212> TYPE: PRT
<213> ORGANISM: Mus musculus

<400> SEQUENCE: 83

Ser Ala Thr
1

<210> SEQ ID NO 84
<211> LENGTH: 3
<212> TYPE: PRT
<213> ORGANISM: Mus musculus

<400> SEQUENCE: 84

Lys Ile Ser
1

<210> SEQ ID NO 85
<211> LENGTH: 3
<212> TYPE: PRT
<213> ORGANISM: Mus musculus

<400> SEQUENCE: 85

Ser Ala Ser
1

<210> SEQ ID NO 86
<211> LENGTH: 3
<212> TYPE: PRT
<213> ORGANISM: Mus musculus

<400> SEQUENCE: 86

Tyr Thr Ser
1

<210> SEQ ID NO 87
<211> LENGTH: 11
<212> TYPE: PRT
<213> ORGANISM: Mus musculus

<400> SEQUENCE: 87

Ala Pro Tyr Asp Tyr Asp Tyr Ala Met Asp Phe
1               5                   10

<210> SEQ ID NO 88
<211> LENGTH: 10
<212> TYPE: PRT
<213> ORGANISM: Mus musculus

<400> SEQUENCE: 88

Ala Arg Trp Asp Tyr Glu Gly Phe Asp Cys
1               5                   10

<210> SEQ ID NO 89
<211> LENGTH: 10
<212> TYPE: PRT
<213> ORGANISM: Mus musculus

<400> SEQUENCE: 89

Ala Arg Trp Asp Tyr Glu Gly Phe Asp Tyr
1               5                   10

<210> SEQ ID NO 90
<211> LENGTH: 11
<212> TYPE: PRT
<213> ORGANISM: Mus musculus

<400> SEQUENCE: 90

Ala Thr Tyr Glu Tyr Asp Val Gly Leu Asp Tyr
1               5                   10

<210> SEQ ID NO 91
<211> LENGTH: 13
<212> TYPE: PRT
<213> ORGANISM: Mus musculus

<400> SEQUENCE: 91

Ala Arg Ser Asp Tyr Asp Tyr Gly Tyr Ala Met Asp Tyr
1               5                   10

<210> SEQ ID NO 92
<211> LENGTH: 14
<212> TYPE: PRT
<213> ORGANISM: Mus musculus

<400> SEQUENCE: 92

Ala Lys Trp Gly Asn Trp Asp Glu Gly Thr Trp Phe Pro Tyr
1               5                   10

<210> SEQ ID NO 93
<211> LENGTH: 11
<212> TYPE: PRT
<213> ORGANISM: Mus musculus

<400> SEQUENCE: 93

Ala Arg Tyr Asn Tyr Glu Gly Tyr Phe Asp Tyr
1               5                   10

<210> SEQ ID NO 94

```
<211> LENGTH: 15
<212> TYPE: PRT
<213> ORGANISM: Mus musculus

<400> SEQUENCE: 94

Ala Ser Leu Tyr Tyr Asp Tyr Glu Arg Asp Tyr Ala Met Asp Tyr
1               5                   10                  15

<210> SEQ ID NO 95
<211> LENGTH: 13
<212> TYPE: PRT
<213> ORGANISM: Mus musculus

<400> SEQUENCE: 95

Ala Ser Phe Tyr Tyr Asp Tyr Asp His Ala Met Asp Tyr
1               5                   10

<210> SEQ ID NO 96
<211> LENGTH: 15
<212> TYPE: PRT
<213> ORGANISM: Mus musculus

<400> SEQUENCE: 96

Ala Ser Phe Tyr Tyr Asp Tyr Asp Arg Gly Ala Ala Met Asp Tyr
1               5                   10                  15

<210> SEQ ID NO 97
<211> LENGTH: 15
<212> TYPE: PRT
<213> ORGANISM: Mus musculus

<400> SEQUENCE: 97

Ala Ser Leu Tyr Tyr Asp Tyr Glu Arg Glu Tyr Gly Met Asp Tyr
1               5                   10                  15

<210> SEQ ID NO 98
<211> LENGTH: 15
<212> TYPE: PRT
<213> ORGANISM: Mus musculus

<400> SEQUENCE: 98

Ala Arg Leu Asp Tyr Thr Asn Tyr Asn Ser Tyr Pro Met Asp Tyr
1               5                   10                  15

<210> SEQ ID NO 99
<211> LENGTH: 9
<212> TYPE: PRT
<213> ORGANISM: Mus musculus

<400> SEQUENCE: 99

Gln His Phe Trp Ser Thr Pro Phe Thr
1               5

<210> SEQ ID NO 100
<211> LENGTH: 9
<212> TYPE: PRT
<213> ORGANISM: Mus musculus

<400> SEQUENCE: 100

Gln Asn Gly His Ser Phe Pro Pro Thr
1               5

<210> SEQ ID NO 101
<211> LENGTH: 9
<212> TYPE: PRT
```

<213> ORGANISM: Mus musculus

<400> SEQUENCE: 101

Gln Gln Tyr Ser Lys Leu Pro Trp Thr
1               5

<210> SEQ ID NO 102
<211> LENGTH: 9
<212> TYPE: PRT
<213> ORGANISM: Mus musculus

<400> SEQUENCE: 102

Gln His Phe Trp Gly Pro Pro Trp Thr
1               5

<210> SEQ ID NO 103
<211> LENGTH: 9
<212> TYPE: PRT
<213> ORGANISM: Mus musculus

<400> SEQUENCE: 103

Phe Gln Gly Ser His Val Pro Trp Thr
1               5

<210> SEQ ID NO 104
<211> LENGTH: 9
<212> TYPE: PRT
<213> ORGANISM: Mus musculus

<400> SEQUENCE: 104

Gln Asn Gly His Ser Phe Pro Leu Thr
1               5

<210> SEQ ID NO 105
<211> LENGTH: 9
<212> TYPE: PRT
<213> ORGANISM: Mus musculus

<400> SEQUENCE: 105

Gln Gln Tyr His Ser Tyr Pro Phe Thr
1               5

<210> SEQ ID NO 106
<211> LENGTH: 9
<212> TYPE: PRT
<213> ORGANISM: Mus musculus

<400> SEQUENCE: 106

Gln Gln Tyr Asn Ser Tyr Pro Phe Thr
1               5

<210> SEQ ID NO 107
<211> LENGTH: 9
<212> TYPE: PRT
<213> ORGANISM: Mus musculus

<400> SEQUENCE: 107

Gln Gln Tyr Asn Ser Tyr Pro Tyr Thr
1               5

<210> SEQ ID NO 108
<211> LENGTH: 9
<212> TYPE: PRT
<213> ORGANISM: Mus musculus

```
<400> SEQUENCE: 108

Gln Gln Tyr Ser Lys Phe Pro Trp Thr
1               5

<210> SEQ ID NO 109
<211> LENGTH: 67
<212> TYPE: PRT
<213> ORGANISM: Artificial Sequence
<220> FEATURE:
<223> OTHER INFORMATION: Engineered

<400> SEQUENCE: 109

Met Ala Gln Gln Cys Phe His Ser Glu Tyr Phe Asp Ser Leu Leu His
1               5                   10                  15

Ala Cys Lys Pro Cys His Leu Arg Cys Ser Asn Pro Pro Ala Thr Cys
            20                  25                  30

Gln Pro Tyr Cys Asp Pro Ser Val Thr Ser Ser Val Lys Gly Thr Tyr
        35                  40                  45

Thr Gly Gly Gly Ser Gly Gly Gly Ser His His His His His His
    50                  55                  60

His His His
65

<210> SEQ ID NO 110
<211> LENGTH: 71
<212> TYPE: PRT
<213> ORGANISM: Artificial Sequence
<220> FEATURE:
<223> OTHER INFORMATION: Engineered

<400> SEQUENCE: 110

Met Leu Gln Met Ala Arg Gln Cys Ser Gln Asn Glu Tyr Phe Asp Ser
1               5                   10                  15

Leu Leu His Asp Cys Lys Pro Cys Gln Leu Arg Cys Ser Ser Thr Pro
            20                  25                  30

Pro Leu Thr Cys Gln Arg Tyr Cys Asn Ala Ser Met Thr Asn Ser Val
        35                  40                  45

Lys Gly Met Asn Ala Gly Gly Gly Ser Gly Gly Gly Ser His His His
    50                  55                  60

His His His His His His His
65                  70
```